US012605341B2

(12) United States Patent
  Camber et al.

(10) Patent No.: US 12,605,341 B2
(45) **Date of Patent: \*Apr. 21, 2026**

(54) DRY POWDER COMPOSITION FOR PERORAL ADMINISTRATION

(71) Applicant: VICORE PHARMA AB, Stockholm (SE)

(72) Inventors: Ola Camber, Stockholm (SE); Arnout Everaert, Mariakerke (BE); Stefan Grudén, Uppsala (SE)

(73) Assignee: VICORE PHARMA AB, Stockholm (SE)

( * ) Notice: Subject to any disclaimer, the term of this patent is extended or adjusted under 35 U.S.C. 154(b) by 166 days.

This patent is subject to a terminal disclaimer.

(21) Appl. No.: 18/491,946

(22) Filed: Oct. 23, 2023

(65) Prior Publication Data

US 2024/0269081 A1      Aug. 15, 2024

Related U.S. Application Data

(63) Continuation of application No. 17/696,984, filed on Mar. 17, 2022, now Pat. No. 11,844,868, which is a continuation of application No. PCT/GB2021/050994, filed on Apr. 23, 2021.

(30) Foreign Application Priority Data

Apr. 24, 2020   (GB) ..................................... 2006079

(51) Int. Cl.
   *A61K 9/48*       (2006.01)
   *A61K 9/00*       (2006.01)
   *C07D 403/08*     (2006.01)
(52) U.S. Cl.
   CPC .......... *A61K 9/4808* (2013.01); *A61K 9/0053* (2013.01); *A61K 9/4816* (2013.01); *A61K 9/485* (2013.01); *A61K 9/4858* (2013.01); *A61K 9/4866* (2013.01); *C07D 403/08* (2013.01)
(58) Field of Classification Search
   None
   See application file for complete search history.

(56) References Cited

U.S. PATENT DOCUMENTS

| | | |
|---|---|---|
| 10,154,990 B2 | 12/2018 | Park et al. |
| 11,654,115 B2 | 5/2023 | Camber et al. |
| 11,819,494 B2 | 11/2023 | Dalsgaard et al. |
| 11,844,868 B2 | 12/2023 | Camber et al. |
| 2008/0139483 A1 | 6/2008 | Gorczynski |
| 2013/0289084 A1 | 10/2013 | Pfleger et al. |

FOREIGN PATENT DOCUMENTS

| | | | |
|---|---|---|---|
| WO | 99/43339 A1 | 9/1999 | |
| WO | 2002/096883 A1 | 12/2002 | |
| WO | 2005/123072 A1 | 12/2005 | |
| WO | WO-2016139475 A1 * | 9/2016 | ............. A61K 45/06 |
| WO | 2017/221012 A1 | 12/2017 | |
| WO | 2019/008393 A1 | 1/2019 | |
| WO | 2019/183513 A1 | 9/2019 | |
| WO | 2020/095042 A1 | 5/2020 | |

OTHER PUBLICATIONS

Rathinasabapathy et al., "The Selective Angiotensin II Type 2 Receptor Agonist, Compound 21, Attenuates the Progression of Lung Fibrosis and Pulmonary Hypertension in an Experimental Model of Bleomycin-Induced Lung Injury," Front. Physiol. 9, Article 180 (2018).
Hashmat et al., "Developmeni of Enteric Coated Flurbiprofen Tablets using Opadryiacryl-eze System—A Technical Note," AAPS PharmaSciTech. 9(1):116-121 (2008).
King et al., "Idiopathic Pulmonary Fbrosis," Lancet 378:1949-1961 (2011).
Noble et al., "Pulmonary Fibrosis: Patterns and Perpetrators," J. Clin. Invest. 122:2756-2762 (2012).
Ley et al., "Clinical Course and Prediction of Survival in IdiopathicPulmonary Fibrosis," Am. J. Respir. Crit. Care Med. 183:431-440 (2011).
Rafii et al., "A Review of Current and Novel Therapies for Idiopathic Pulmonary Fibrosis," J. Thorac. Dis. 5:48-73 (2013).
De Gasparo et al., "International Union of Pharmacology. XXIII. The Angiotensin II Receptors," Pharmacol. Rev. 52:415-472 (2000).
Lawrence and Bing, "FDA Bioequivalence Standards" AAPS Advances in the Pharmaceutical Sciences Series 13. Springer New York Heidelberg Dordrecht London.
International Preliminary Report on Patentability for PCT/GB2021/050994, dated Feb. 28, 2022.
Itai, "Our Products and Dosage Forms," Pharmacia 40(9):822-826 (2004) (with Machine Translation).
Tokunaga, "Formulation Development From a Generic Perspective," Pharmacia 52(5):417-421 (2016) (with Machine Translation).

(Continued)

*Primary Examiner* — Susan T Tran
(74) *Attorney, Agent, or Firm* — Troutman Pepper Locke LLP (Rochester)

(57) ABSTRACT

There is provided a pharmaceutical dosage form that is suitable for peroral administration to the gastrointestinal tract, which dosage form comprises a pharmaceutical composition in the form of a particulate mixture comprising solid particles of N-butyloxycarbonyl-3-(4-imidazol-1-ylmethylphenyl)-5-iso-butylthiophene-2-sulfonamide (C21), or a pharmaceutically-acceptable salt thereof, admixed with a blend of carrier particles with weight- and/or a volume-based mean diameter, and/or a structural/particle density, that is/are similar to the weight- and/or volume-based mean diameter, and/or the structural/particle density, of the solid particles of C21, and a glidant, which composition is contained within a capsule that is suitable for such peroral administration. Preferred carrier particles have a weight- and/or a volume-based mean diameter that is less than about 100 μm. Preferred carrier particle materials include mannitol. Preferred glidants comprise colloidal silica. Such dosage forms find utility in the treatment of lung diseases, such as idiopathic pulmonary fibrosis, sarcoidosis and respiratory virus-induced tissue damage.

17 Claims, 1 Drawing Sheet

(56)        References Cited

OTHER PUBLICATIONS

Office Action in U.S. Appl. No. 17/696,984, mailed Jun. 27, 2022.
Office Action in U.S. Appl. No. 17/696,984, mailed Oct. 19, 2022.

* cited by examiner

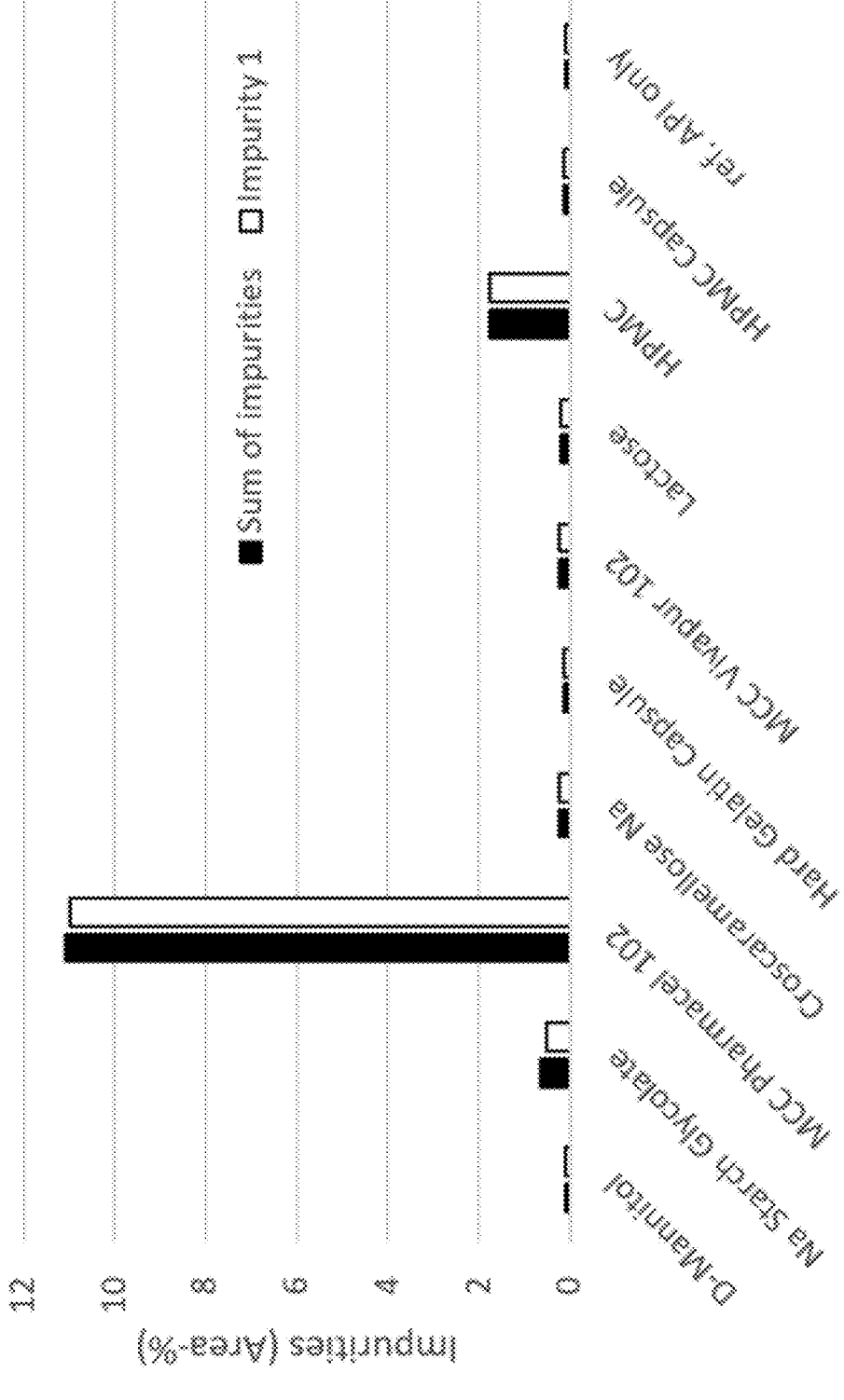

DRY POWDER COMPOSITION FOR PERORAL ADMINISTRATION

This application is a continuation of U.S. patent application Ser. No. 17/696,984, filed Mar. 17, 2022, which is a continuation of PCT/GB2021/050994, filed Apr. 23, 2021, which is hereby incorporated by reference in its entirety, and which claims priority benefit of GB 2006079.4, filed Apr. 24, 2020.

FIELD OF THE INVENTION

This invention relates to new pharmaceutical dosage forms, their use as medicaments and particularly to their administration to treat, inter alia, lung diseases, for example interstitial lung diseases.

BACKGROUND AND PRIOR ART

Interstitial lung diseases (ILDs) are a group of lung diseases that affect the interstitium, characterized by tissue around alveoli becoming scarred and/or thickened, and so inhibiting the respiratory process.

ILDs are distinct from obstructive airway diseases (e.g. chronic obstructive airway disease (COPD) and asthma), which are typically characterized by narrowing (obstruction) of bronchi and/or bronchioles. ILDs may be caused by injury to the lungs, which triggers an abnormal healing response but, in some cases, these diseases have no known cause. ILDs can be triggered by chemicals (silicosis, asbestosis, certain drugs), infection (e.g. pneumonia) or other diseases (e.g. rheumatoid arthritis, systemic sclerosis, myositis, hypersensitivity pneumonitis or systemic lupus erythematosus).

The most common ILDs are idiopathic pulmonary fibrosis (IPF) and sarcoidosis, both of which are characterized by chronic inflammation and reduced lung function.

Sarcoidosis is a disease of unknown cause that is characterized by collections of inflammatory cells that form lumps (granulomas), often beginning in the lungs (as well as the skin and/or lymph nodes, although any organ can be affected). When sarcoidosis affects the lungs, symptoms include coughing, wheezing, shortness of breath, and/or chest pain.

Treatments for sarcoidosis are patient-specific. In most cases, symptomatic treatment with non-steroidal anti-inflammatory drugs (NSAIDs) is possible, but for those presenting lung symptoms, glucocorticoids (e.g. prednisone or prednisolone), antimetabolites and/or monoclonal anti-tumor necrosis factor antibodies are often employed.

IPF is a lung-disease of unknown cause that affects about 5 million people globally. It has no curative treatment options except, in rare cases, lung transplantation, resulting in a chronic, irreversible, progressive deterioration in lung function and, in most cases, leading to death within 2-5 years (median survival 2.5 to 3.5 years). While the overall prognosis is poor in IPF, it is difficult to predict the rate of progression in individual patients. Risk factors for IPF include age, male gender, genetic predisposition and history of cigarette smoking. The annual incidence is between 5-16 per 100,000 individuals, with a prevalence of 13-20 cases per 100,000 people, increasing dramatically with age (King Jr T E et al., Lancet (2011) 378, 1949-1961; Noble P W et al., J. Clin. Invest. (2012) 122, 2756-2762). IPF is limited to the lungs and is recalcitrant to therapies that target the immune system which distinguishes it from pulmonary fibrosis (PF) associated with systemic diseases.

Patients with IPF usually seek medical assistance due to chronic and progressive exertional dyspnea and cough. Imaging of the lung classically reveals traction bronchiectasis, thickened interlobar septae and subpleural honeycombing. When all three manifestations are present and there is no evidence of a systemic connective tissue disease or environmental exposure, a diagnosis of IPF is very likely. A definite diagnosis is usually made by lung biopsy and requires a multidisciplinary team of expertise including pulmonologists, radiologists and pathologists experienced in ILDs.

IPF demonstrates different phenotypes with different prognosis, defined as mild, moderate and severe. Mild cases follow a stable or slow progressive path with patients sometimes taking several years to seek medical advice. Accelerated IPF has a much more rapid progression with shortened survival, affecting a sub-group of patients, usually male cigarette smokers. Acute exacerbations of IPF are defined as a rapid worsening of the disease, and patients in this sub-population have very poor outcomes with a high mortality rate in the short run. The cause of IPF is unknown but it appears to be a disorder likely arising from an interplay of environmental and genetic factors resulting in fibroblast driven unrelenting tissue remodeling rather than normal repair; a pathogenesis primarily driven by fibrosis rather than inflammation. A growing body of evidence suggests that the disease is initiated through alveolar epithelial cell microinjuries and apoptosis, activating neighboring epithelial cells and attracting stem or progenitor cells that produce the factors responsible for the expansion of the fibroblast and myofibroblast populations in a tumor like way. The fibroblastic foci secrete exaggerated amounts of extracellular matrix that destroys the lung parenchyma and ultimately leads to loss of lung function.

The mean annual rate of decline in lung function (vital capacity) is within a range of 0.13-0.21 litres. Symptoms precede diagnosis by 1-2 years and radiographic signs may precede symptoms (Ley B et al., Am. J. Respir. Crit. Care Med. (2011) 183, 431-440).

Numerous treatment approaches have been tested in preclinical models and clinical trials such as anti-inflammatory, immune-modulatory, cytotoxic, general anti-fibrotic, anti-oxidant, anti-coagulant, anti-chemokine, anti-angiogenic drugs as well as RAS-blockers, endothelin antagonists, and sildenafil, all of which have basically been shown to provide limited or no benefits (Rafii R et al., J. Thorac. Dis. (2013) 5, 48-73).

Current treatment of IPF includes oxygen supplementation. Medications that are used include pirfenidone or nintedanib, but only with limited success in slowing the progression of the disease. Further, both of these drugs commonly cause (predominantly gastrointestinal) side-effects.

There are drawbacks associated with all of the aforementioned ILD (and IPF) drug treatments and there is a real clinical need for safer and/or more effective treatments.

To restore the alveolar epithelium is very desirable as a therapeutic effect in IPF, and therefore stem cell therapy has also been tested. Some preclinical studies have shown promise in the use of pluripotent stem cells that can differentiate into lung epithelial and endothelial cells, thereby repairing lung injury and fibrosis.

Currently, a lung transplant is the only intervention that substantially improves survival in IPF patients. However, complications such as infections and transplant rejection are not uncommon.

The development of new treatment strategies for IPF is therefore important. Thus, the fundamental challenge for the future is to develop appropriate therapeutic approaches that will reverse or stop the progression of the disease.

The Renin-Angiotensin System (RAS) is a key regulator of blood pressure homeostasis. Renin, a protease, cleaves its only known substrate (angiotensinogen) to form angiotensin I (Ang I), which in turn serves as substrate to angiotensin converting enzyme (ACE) to form Ang II. The endogenous hormone Ang II is a linear octapeptide ($Asp^1$-$Arg^2$-$Val^3$-$Tyr^4$-$Ile^5$-$His^6$-$Pro^7$-$Phe^8$), and is an active component of the renin angiotensin system (RAS).

The angiotensin II type 1 (AT1) receptor is expressed in most organs, and is believed to be responsible for the majority of the pathological effects of Ang II. The safety and efficacy of losartan (an AT1-receptor inhibitor) has recently been investigated in a small uncontrolled open-label pilot trial on IPF (www.clinicaltrials.gov identifier NCT00879879).

Several studies in adult individuals appear to demonstrate that, in the modulation of the response following Ang II stimulation, activation of the angiotensin II type 1 (AT2) receptor has opposing effects to those mediated by the AT1 receptor.

The AT2 receptor has also been shown to be involved in apoptosis and inhibition of cell proliferation (de Gasparo M et al., Pharmacol. Rev., 2000; 52:415-472).

AT2 receptor agonists have also been shown to be of potential utility in the treatment and/or prophylaxis of disorders of the alimentary tract, such as dyspepsia and irritable bowel syndrome, as well as multiple organ failure (see international patent application WO 99/43339).

The expected pharmacological effects of agonism of the AT2 receptor are described in general in de Gasparo M et al., supra. It is not mentioned that agonism of the AT2 receptor may be used to treat IPF.

International patent application WO 2002/096883 describes the preparation of imidazolyl, triazolyl, and tetrazolyl thiophene sulfonamides and derivatives as AT2 receptor agonists. Of the compounds described in that document (as Example 1) is N-butyloxycarbonyl-3-(4-imidazol-1-yl-methylphenyl)-5-iso-butylthiophene-2-sulfonamide (Compound 21 or, as used hereinafter 'C21'), which was selected for clinical development from a group of about 20 related analogues as a selective AT2 receptor agonist. C21 is now in clinical development for treatment of AT2 receptor related disorders in which treatment with an AT2 receptor agonist is believed to be beneficial including IPF (see, for example, international patent application WO 2016/139475).

Formulative work carried out in respect of C21 and salts thereof has proven extremely difficult. Part of the issue is the hitherto unreported extreme sensitivity of C21 and salts thereof to the combined presence of light and water. Furthermore, attempts to provide stable solid state formulations, even in the dry state, have produced blends with conventional excipients that are chemically unstable. These pieces of information have not been made available to the public previously.

As a consequence, C21 has previously been formulated as an aqueous solution, which is frozen whilst stored and then thawed immediately prior to peroral dosing. Protecting C21 in this way from light-catalyzed aqueous decomposition presents logistic issues as far as shipping drug product around the world is concerned. A more stable, pharmaceutically-acceptable composition is highly desirable, if not a requirement, for a commercially-viable product.

The applicant has been working with this active ingredient for nearly 20 years, and, until recently, has not managed to obtain a pharmaceutically-acceptable dosage form, that is one in which the active ingredient is stable when stored at ambient temperatures, in a reproducible way.

In attempting to prepare such an improved peroral capsule-based dosage form, the applicant has found that it is possible to solve the above problems by dry blending with specific combination of excipients, in a specific manner, as described hereinafter.

BRIEF DESCRIPTION OF THE DRAWING

FIG. 1 shows the instability of C21 sodium salt in the presence of numerous standard excipients.

DISCLOSURE OF THE INVENTION

According to a first aspect of the invention, there is provided a pharmaceutical dosage form that is suitable for peroral administration to the gastrointestinal tract, which dosage form comprises a pharmaceutical composition in the form of a particulate mixture comprising solid particles of C21, or a pharmaceutically-acceptable salt thereof, admixed with a blend of carrier particles with a weight- and/or a volume-based mean diameter, and/or a structural (particle) density, that is/are similar to the weight- and/or volume-based mean diameter, and/or the structural (particle) density, respectively, of the solid particles of C21, or a pharmaceutically-acceptable salt thereof, and a glidant, which composition is contained within a capsule that is suitable for such peroral administration. Such dosage forms are hereinafter referred to together as 'the dosage forms of the invention'.

Dosage forms of the invention are suitable for peroral administration and delivery, as a complete dosage form, to the gastrointestinal tract. This means that a dosage form of the invention should be suitable for swallowing as a whole, complete dosage form for subsequent consumption and/or ingestion within the gastrointestinal tract, and, in use, is swallowed and then consumed and/or ingested within that tract.

Appropriate pharmaceutically-acceptable capsules include soft-shell or hard-shell capsules, which can be made from gelatin, cellulose polymers, e.g. hydroxypropyl methylcellulose (HPMC or hypromellose), hypromellose acetate succinate (HPMCAS), starch polymers, pullulan or other suitable materials, for example by way of standard capsule filling processes.

However, we prefer that the capsules are hard-shell, two-piece capsules, for example capsules that are made from gelatin or, more preferably, HPMC and are supplied as closed halves that may be separated and filled with particulate matter, followed by re-assembly. Such capsules may be of any size (e.g. 00 to 5), but preferred capsule sizes are size 2, size 1 or, more preferably, size 0.

It is further preferred that the pharmaceutical composition of the dosage form of the invention, which is contained within a capsule as described above, is manufactured and/or stored in a manner in which it is kept essentially free of water.

By 'essentially free of water', we include that appropriate precautions are taken to ensure that both particles of C21 or salt thereof, and the particles of essential excipients with which it is mixed, are individually prepared and/or provided in a manner in which they are essentially dry, and are also mixed together to form dry mixture in an environment in which they are kept essentially dry.

By 'essentially dry' or 'essentially free of water', we include that the composition comprising C21/salt and essential excipients comprises, as a whole, no more that about 5%, including no more than about 2%, such as no more than about 1%, including no more than about 0.5%, such as about 0.1% water or less.

Compositions of the dosage forms of the invention comprising C21 or salt thereof and essential excipients as hereinbefore defined may, once prepared, be thereafter loaded into capsules. In view of the fact that it is preferred that such compositions are prepared in an essentially water-free state, such loading also preferably takes place in a manner in which it is kept in such a state.

In this respect, although pharmaceutically-acceptable capsule materials may contain residual amount of water, ingress of water into the composition from the capsule material should be minimised, so protecting the highly sensitive C21 or salt thereof from contact with water and therefore, in the presence of light, degradation.

It is nevertheless preferred (although not necessarily essential) to package dosage forms of the invention in a manner that keeps the dosage form itself dry and protected from light. This may include hermetically-sealed packaging, use of deliquescent materials, etc.

C21 or salt thereof is presented in the form of particles, which may be amorphous or crystalline or a mixture of the two. Preferred particles are of a size that will not lead to segregation, either during formation of the composition to be loaded into capsules during the capsule-loading process or upon storage.

In this respect, C21 or salt thereof may be provided in the form of a plurality of primary (i.e. non-agglomerated) particles typically having a weight- and/or a volume-based mean diameter of no more than about 1,000 μm, such as about 500 μm, including about 250 μm, preferably no more than about 100 μm, including no more than about 50 μm, such as about 20 μm, or no more than about 10 μm. Although there is no lower limit on particle sizes that may be employed in accordance with the invention, for ease of manufacture, we prefer that primary particles of C21 or salt thereof have weight- and/or volume-based mean diameter of no less than about 1 μm, such as about 2 μm, including about 3 μm.

As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. Particle sizes may also be measured by standard equipment, such as a dry particle size measurement technique, including dry dispersion technologies available from manufacturers such as Sympatec GmbH (Clausthal-Zellerfeld, Germany). Other instruments that are well known in the field may be employed to measure particle size, such as equipment sold by e.g. Malvern Instruments, Ltd. (Worcestershire, UK), Shimadzu (Kyoto, Japan) and (Elzone, Micromeritics (USA; electrical sensing zone method).

By particles having weight- and/or volume-based mean diameters within the above limits, we include mean diameters of particles when prepared and prior to mixing with the essential excipients according to the invention, and/or prior to being loaded into capsules. It will be appreciated that some aggregation of primary particles to form secondary particles may occur during handling and/or processing of active ingredient. This should nevertheless be minimised.

C21 or salt thereof may also be provided in the form of particles with a relative narrow particle size distribution (PSD), as measured by standard techniques and art-accepted parameters, including mass median diameter ($D_{50}$; the log-normal mass median diameter), the average particle size by mass and/or the diameter at which 50% of the mass in the cumulative PSD are contained) and/or geometric standard deviation (GSD or $\sigma_g$ as measured by the formula $D_{84.13}/D_{50}$ or $D_{50}/D_{15.78}$, where $D_{84.13}$ and $D_{15.78}$ are respectively the diameters at which 84.13% and 15.78% of the mass are contained, and $D_{50}$ is as hereinbefore defined). Such parameters may be measured and calculated in-process using any appropriate sampling method and particle size measurement technique as described hereinbefore.

It is preferred in this respect that C21 or salt thereof has a PSD with a GSD that is less than about 4, such as less than about 3.

Primary particles of C21 or salt thereof may be prepared by an appropriate technique, such as precipitation, cutting (e.g. by way of dissolution in a supercritical fluid under pressure, followed by rapid expansion), spray drying, or may, if appropriate, be micronized by techniques that are well known to those skilled in the art, such as grinding, dry milling, jet milling, wet milling and/or crushing.

Particles may also be sieved to separate into a desired size fraction, and/or screened to break up agglomerates and/or remove fine material. In either case, unused undersized (fine), and oversized, material may be reworked to avoid waste. Alternatively, particles may be separated into appropriate particle sizes using cyclonic separation, by way of an air classifier, sedimentation, force-field fractionation and/or elutriation.

Although C21 or salt thereof may be selected and/or provided with the aforementioned weight- or volume-based mean diameters, particle sizes, PSDs and/or GSDs using one or more of the above techniques, one of the primary benefits of formulating the compositions that are to be loaded into capsules to form dosage forms of the invention, is that C21 or salt thereof does not require the particle processing techniques that are described above prior to blending with the essential excipients.

As mentioned hereinbefore, we have found that C21 and salts thereof are extremely difficult materials to work with. In particular, and as described hereinafter, compatibility studies have revealed that certain standard excipients, when co-mixed with C21 and salts thereof give rise to significant chemical instability of the active ingredient. Furthermore, C21 and salts thereof are formed as needle-like crystals that are sticky and have a tendency to agglomerate. This means that dry mixing with other standard pharmaceutically-acceptable ingredients is very difficult, and it is not straightforward to produce blends with pharmaceutically-acceptable content uniformities of active ingredient, and/or dose uniformities the same within capsules.

Further, as described hereinafter, micronizing primary particles of active ingredient has also not provided a solution to these problems, as the skilled person might have expected to be the case, and has also been found to give rise to additional problems connected with localised heating and static electricity.

However, we have found that by blending C21 or pharmaceutically-acceptable salt thereof with a pre-mixed blend of:

(a) carrier particles having weight- and/or a volume-based mean diameter that is around the same dimension that of the C21/salt particles, and (b) a glidant, it is possible to avoid the aforementioned problems and to provide a composition for loading into capsules in which C21 or salt thereof is not only homogeneously and evenly distributed, ensuring dose homogeneity of active ingredient between capsules following such loading, but is also physically and chemically stable, during and/or after manufacture, under normal storage conditions, and/or during use.

The terms 'homogeneous' and 'distributed homogeneously' in the context of the invention mean that there is a substantially uniform content of C21 or salt thereof throughout the carrier material (and/or other excipients that is/are employed). In other words, if multiple (e.g. at least, 2, more preferably about 6, such as about 10 up to about 30 or more if needed) samples are taken from a mixture comprising active ingredient and carrier blend, the measured content of active ingredient that is present as between such samples gives rise to a standard deviation from the mean amount (i.e. the coefficient of variation and/or relative standard deviation) of less than about 8%, such as less than about 6%, for example less than about 5%, particularly less than about 4%, e.g. less than about 3% and preferably less than about 2%.

Thus, in accordance with the invention, C21 or pharmaceutically-acceptable salt thereof may be made and stored in the form of a composition that may be directly loaded into capsules to make a dosage form of the invention, and furthermore, once made, dosage forms of the invention may be stored under normal storage conditions, with an insignificant degree of changes in physico-chemical properties of the dosage form, composition mixture contained therein and/or, most importantly, active ingredient, over time.

An 'insignificant degree of changes in physico-chemical properties' thus includes that compositions comprising C21/salt admixed with the essential excipients as hereinbefore described, before having been loaded into capsules and after (i.e. in the form of a dosage form of the invention), possess both physical stability and chemical stability.

By 'chemical stability', we include that dry mixture compositions comprising C21/salt and essential excipients of the invention, and dosage forms of the invention, may be stored (with or without appropriate pharmaceutical packaging), under normal storage conditions, with an insignificant degree of chemical degradation or decomposition of the dosage forms of the invention, the dry mixtures contained therein and, particularly, the active ingredient.

By 'physical stability', we include that dry mixture compositions comprising C21/salt and essential excipients of the invention, and dosage forms of the invention, may be stored (with or without appropriate pharmaceutical packaging), under normal storage conditions, with an insignificant degree of physical transformation, such as aggregation, separation or segregation, and/or changes in the nature and/or integrity of the dosage forms of the invention, the dry mixtures contained therein and, particularly, the active ingredient, including solid state phase transition, etc.

Examples of 'normal storage conditions' include temperatures of between minus 80 and plus 50° C. (preferably between 0 and 40° C. and more preferably ambient temperature, such as between 15 and 30° C.), pressures of between 0.1 and 2 bars (preferably atmospheric pressure), relative humidities of between 5 and 95% (preferably 10 to 60%), and/or exposure to 460 lux of UV/visible light, for prolonged periods (i.e. greater than or equal to six months).

Under such conditions, C21, salt thereof, and/or dry mix compositions containing them, may be found to be less than about 15%, more preferably less than about 10%, and especially less than about 5%, physically and/or chemically transformed as hereinbefore defined. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

The essential excipients that are admixed with particles of C21 or pharmaceutically-acceptable salt thereof, comprise a blend of carrier particles with weight- and/or a volume-based mean diameter that is about the same as the C21/salt particles, and a glidant.

Suitable carrier particle materials may comprise pharmaceutically-acceptable substances that are soluble in water, such as carbohydrates, e.g. sugars, such as lactose, and sugar alcohols, such as mannitol, sorbitol and xylitol; or pharmaceutically-acceptable inorganic salts, such as sodium chloride. Alternatively, carrier particles may comprise pharmaceutically-acceptable substances that are insoluble or sparingly soluble in water, such as microcrystalline cellulose, dicalcium phosphate anhydrate, dicalcium phosphate dihydrate, tricalcium phosphate, calcium carbonate, and barium sulphate; starch and pre-gelatinised starch. Preferred carrier particle materials include carbohydrates, including sugar alcohols, such as sorbitol, xylitol and, particularly, mannitol. Carrier particles may comprise physical mixtures of any of these materials and/or may comprise composites of one or more of these materials.

The carrier particles have a similar particle size distribution and/or structural (particle) density as the active ingredient particles that are employed in compositions to be loaded into capsules to make dosage forms of the invention.

By 'similar particle size distribution and/or structural (particle) density' we mean that the weight- and/or volume-based mean diameter, and/or particle density, of the carrier particles is within about +75%, such as about +50%, including about +40%, e.g. about +30%, or about +20% including about +10% of the relevant dimensions of the C21 or salt thereof that is employed.

In this respect, preferred carrier particle sizes include weight- and/or a volume-based mean diameter that are less than about 100 μm, including less than about 80 μm, such as less than about 70 μm, for example between about 20 μm and about 60 μm (e.g. about 25 μm or, more preferably, about 50 μm).

We have found that, by employing carrier particles with sizes that are similar to those of the active ingredient and/or within the above ranges, blend segregation is avoided.

In order to make dry mix compositions to be loaded into capsules to make dosage forms of the invention, prior to mixing with active ingredient, carrier particles of the requisite size are pre-blended with a suitable glidant material. A glidant is a pharmaceutically-acceptable material that will promote powder flow by reducing interparticle friction and/or cohesion (but does not necessarily have an ability to reduce and/or prevent adhesion to external materials, such as capsule filling machines or hoppers). Suitable pharmaceutically-acceptable glidant materials thus include talc, magnesium carbonate or calcium silicate, although it is preferred that the glidant is a hydrophilic glidant, such as one or more of the various forms of silica, including silica gels, silica aerogels or, more particularly, a proprietary silica produced under registered trademark 'Syloid®' (see https://grace-.com/pharma-and-biotech/en-us/Documents/Syloid/M309c), a colloidal silica, and/or fumed/pyrogenic silica. Preferred forms of silica thus include stable aqueous dispersions (sols) of amorphous silica particles with a weight- and/or a volume-based mean diameter that is between about 1 nm and about 100 nm (e.g. up to about 50 nm, such as up to about 20 nm, such as between about 10 nm and about 15 nm).

It is preferred therefore that the glidant and the carrier particles are mixed together to form an interactive (or an ordered) mixture of carrier particles that are largely coated with smaller particles of a glidant material, which blend is then admixed with active ingredient particles.

We have also found that by adding the aforementioned glidant to the carrier particles to first form an excipient blend, prior to mixing with active ingredient, this improves the flow properties of that excipient blend, and so leads subsequently to better mixing with C21 or pharmaceutically-acceptable salt thereof, further decreasing the likelihood of blend segregation.

Dosage forms of the invention may also include other excipients that are well known to those skilled in the art for peroral delivery of active ingredients. Other excipients may thus be added, if required, to the powder blend according to the invention, such as dyestuffs, antioxidants, which may be naturally occurring or otherwise (e.g. butylated hydroxytoluene (BHT), vitamin C, vitamin E, β-carotene, uric acid, uniquion, superoxide dismutase (SOD), glutathione peroxidase or peroxidase catalase), preservatives and disintegrants, including those described in for example, Rowe et al., Handbook of Pharmaceutical Excipients, $8^{th}$ ed. (2017).

However, in view of the extreme sensitivity of C21 and salts thereof to other chemicals, it is preferred that such other excipients are not included in dosage forms of the invention. In this respect, there is provided a dosage form of the invention consisting essentially of a pharmaceutical composition in the form of a particulate mixture comprising solid particles of C21, or a pharmaceutically-acceptable salt thereof, admixed with a blend of carrier particles with a weight- and/or a volume-based mean diameter, and/or a structural (particle) density, that is/are similar to the weight- and/or volume-based mean diameter, and/or the structural (particle) density, of the solid particles of C21, or a pharmaceutically-acceptable salt thereof (as hereinbefore defined), and glidant, which composition is contained within a capsule that is suitable for such peroral administration. All preferred features mentioned herein for other aspects of the invention which relate in any way to this aspect of the invention are equally applicable.

The term 'consisting essentially of' will be understood to mean that the scope of this (and only this) aspect of the invention is limited to the specified essential features mentioned above, along with other features that do not materially affect the basic and novel characteristic(s) of this aspect of the invention.

In this respect, although not an essential feature of the invention, it may be preferable to add a lubricant (such as sodium stearyl fumarate or, preferably, magnesium stearate) to the blend prior to filling into capsules, in order to prevent the blend from adhering to equipment (e.g. capsule filling machines and hoppers). This is a preferred feature that does not materially affect the basic and novel characteristics of this aspect of the invention.

Alternatively, compositions to be loaded into a capsule that 'consist essentially of' a particulate mixture comprising solid particles of C21, or pharmaceutically-acceptable salt thereof admixed with the blend of carrier particles and glidant may mean that the composition comprises at least about 95%, such as at least about 97% by weight of those particular ingredients in total.

Furthermore, dosage forms of the invention may also impart, or may be modified to impart, an immediate, or a modified, release of active ingredient(s).

Additional excipients may be commercially-available or otherwise are described in the literature, for example, Remington The Science and Practice of Pharmacy, 21st ed., Lippincott Williams and Wilkins, Philadelphia (2006) and the documents referred to therein, the relevant disclosures in all of which documents are hereby incorporated by reference. Otherwise, the preparation of suitable peroral formulations may be achieved non-inventively by the skilled person using routine techniques.

Preferred mixing equipment include standard mixing equipment, such as tumbler, shaker mixing (e.g. Turbula), convective, hopper, and fluidization blenders. Preferred blenders include V-blenders.

According to a further aspect of the invention there is provided a process for the production of a dosage form of the invention, which process comprises:

(a) mixing together the carrier particles as hereinbefore defined and the glidant;

(b) mixing the blend from step (a) with the particles of C21 or a pharmaceutically-acceptable salt thereof; and (c) loading the mixture from step (b) into a capsule that is suitable for peroral administration.

It is preferred that the dry mix blend is passed through a sieve at points during the mixing process in order to break up agglomerates that are formed during the blending process, for example as described hereinafter. A suitable sieve is one that has a pore size that is of a size that is as small (or thereabouts) as the particle size of the largest component of the blend. Thus, suitable sieve sizes are about 50 μm, e.g. 75 μm, including 100 μm, such as 150 μm, 200 μm or 250 μm (e.g. about 300 μm) up to about 1,000 μm, such as about 400 μm (e.g. about 500 μm) up to about 900 μm (e.g. about 800 μm).

Pharmaceutically-acceptable salts of C21 include acid addition salts. Such salts may be formed by conventional means, for example by reaction of C21 in the form of the free acid (hereinafter 'free C21') with one or more equivalents of an appropriate acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin. Preferred salts of C21 include HCl salts, alkaline earth salts, such as magnesium and calcium salts, and alkali metal salts, such as potassium or, preferably, sodium salts.

The amount of C21 or salt thereof in a dosage form of the invention will depend, and/or may be selected depending, upon on the severity of the condition, or the expectation of such severity, as well as on the patient, to be treated, but may be determined by the skilled person. The mode of administration may also be determined by the timing and frequency of administration, as well as the severity of the condition.

Suitable lower daily doses of C21 in adult patients (average weight e.g. 70 kg), may be about 10 mg, such as about 20 mg, for example about 25 mg, per day. Suitable upper limits of daily dose ranges of C21 may be up to about 900 mg, such as about 600 mg, including about 400 mg and about 200 mg, such as about 100 mg, and including about 50 mg.

All of the above doses are calculated as free C21. Doses may be split into multiple individual doses per day. Doses may be given between once and six, such as four times daily, preferably three times daily and more preferably twice daily.

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

The dose administered to a patient, in the context of the present invention should be sufficient to effect an appropriate response in the patient over a reasonable timeframe (as described hereinbefore). One skilled in the art will recognize that the selection of the exact dose and composition and the most appropriate delivery regimen will also be influenced by inter alia the pharmacological properties of the formulation, the nature, stage and/or severity of the condition being treated, the physical condition and mental acuity of the recipient, including the age, condition, body weight, sex and response of the patient to be treated, and the stage/severity of the disease, and genetic differences between patients.

Dosage forms of the invention are useful in conditions where AT2 receptors are expressed and their stimulation is desired or required.

In this respect, dosage forms of the invention are indicated in the treatment of conditions characterised by vasoconstriction, fibrosis, inflammation, increased cell growth and/or differentiation, increased cardiac contractility, increased cardiovascular hypertrophy, and/or increased fluid and electrolyte retention, as well as skin disorders and musculoskeletal disorders.

Dosage forms of the invention are particularly indicated in the treatment and/or prevention of ILDs, such as sarcoidosis or fibrosis, more specifically PF and particularly IPF, as well as conditions that may trigger ILDs, such as systemic sclerosis, rheumatoid arthritis, myositis or systemic lupus erythematosus, or are otherwise associated with ILDs, such as pulmonary hypertension and/or pulmonary arterial hypertension.

Dosage forms of the invention may also exhibit thromboxane receptor activity. In this respect, dosage forms of the invention may have an inhibitory effect on platelet activation and/or aggregation (and thus e.g. an antithrombotic effect), and/or may reduce vasoconstriction and/or bronchoconstriction in a therapeutic manner.

Dosage forms of the invention are further indicated in the treatment of stress-related disorders, and/or in the improvement of microcirculation and/or mucosa-protective mechanisms.

Thus, dosage forms of the invention are expected to be useful in the treatment of disorders, which may be characterised as indicated above, and which are of, for example, the gastrointestinal tract, the cardiovascular system, the respiratory tract, the kidneys, the immune system, the eyes, the female reproductive (ovulation) system and the central nervous system (CNS).

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the bilary tract, coelicia, Crohn's disease, ulcerative colitis, diarrhoea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension, and adult respiratory distress syndrome.

Disorders of the kidneys that may be mentioned include renal failure, diabetic nephropathy, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction and endometriosis.

Cardiovascular disorders that may be mentioned include hypertension, cardiac hypertrophy, cardiac failure (including heart failure with preserved ejection fraction), artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction, multiple sclerosis (MS), Alzheimer's disease and Parkinson's disease.

Dosage forms of the invention may also be useful in the modulation of growth metabolism and proliferation, for example in the treatment of ageing, hypertrophic disorders, prostate hyperplasia, autoimmune disorders (e.g. arthritis, such as rheumatoid arthritis, or systemic lupus erythematosus), psoriasis, obesity, neuronal regeneration, the healing of ulcers, inhibition of adipose tissue hyperplasia, stem cell differentiation and proliferation, fibrotic disorders, cancer (e.g. in, or of, the gastrointestinal tract (including the oesophagus or the stomach), the prostate, the breast, the liver, the kidneys, as well as lymphatic cancer, lung cancer, ovarian cancer, pancreatic cancer, hematologic malignancies, etc.), apoptosis, tumours (generally) and hypertrophy, diabetes, neuronal lesions and organ rejection.

Dosage forms of the invention are also useful in the treatment of stroke, spinal cord injury, sickle cell disease, muscular dystrophy, cancer treatment-related cardiotoxicity, peripheral neuropathy and, in particular, systemic sclerosis.

In addition, dosage forms of the invention may be useful in the treatment of respiratory virus-induced tissue damage, which damage may include injury and/or dysfunction of relevant tissues. Relevant tissues include (e.g. mucosal) tissues of the respiratory tract, and especially those of the lung. Relevant tissue thus includes the respiratory epithelium, which moistens the airways and protects against invasion of pathogens such as viruses.

Respiratory viruses that may be mentioned in this respect include influenza viruses, such as influenza A virus (e.g. H1N1 and H3N2 viruses), influenza B virus or influenza C virus), and, more particularly, coronaviruses, including severe acute respiratory syndrome (SARS) coronaviruses, such as SARS coronavirus (SARS-COV) and, particularly, the novel SARS coronavirus 2 (SARS-CoV-2, previously known as '2019-nCOV' or 'novel coronavirus 2019'), which is the virus that causes coronavirus disease 2019 (COVID-19), of which there are many genetic variants.

By 'treatment of tissue damage', we include that C21 and salts thereof may not only have a beneficial effect on tissue damage in the respiratory tract that has been caused by such a virus, but that it may also prevent and/or mitigate the damage that would otherwise have been caused by that virus in the respiratory tract, which occurs when the relevant virus enters e.g. epithelial cells in the respiratory tract.

Thus, C21 and salts thereof may abrogate or prevent the development of diseases that are caused by such virally-induced tissue damage and/or the symptoms of such damage or diseases.

In this respect, C21 and salts thereof may treat, and/or arrest the progress of, diseases that are being, or have been, caused by respiratory viruses (i.e. diseases such as influenza, as well as acute lung injury acute lung injury (ALI), acute respiratory distress syndrome (ARDS), particularly SARS and, more particularly, COVID-19) and their sequelae. C21 and salts thereof may also treat and/or prevent the damage that is being, or has been, caused by such viruses, which includes treating and/or preventing the symptoms of such respiratory diseases, which symptoms include cough, dysp-nea, respiratory distress (as manifest by e.g. the need for supplementary/supplemental oxygen (which may be admin-istered by a face mask or via nasal cannula (high flow or otherwise)), and/or mechanical ventilation/extra-corporeal membrane oxygenation), respiratory failure, and/or pneu-monia, which may occur directly (viral pneumonia) and/or indirectly (bacterial pneumonia resulting from secondary bacterial infections, which is common in influenza), as well as subsequent fibrosis resulting from inflammation in the lungs and other organs (e.g. the heart and kidneys). Further, C21 and salts thereof may prevent or arrest the progress of respiratory virus-induced morbidity and/or mortality, and C21 may treat, and/or arrest the development of any of the chronic symptoms identified above.

In addition, dosage forms of the invention may also be useful in the treatment or prevention of any fibrotic condi-tion of one or more internal organs characterised by the excessive accumulation of fibrous connective tissue, and/or in the treatment or prevention of fibrogenesis and the morbidity and mortality that may be associated therewith. Such fibrosis may be associated with an acute inflammatory condition, such as acute respiratory distress syndrome (ARDS), SARS, and multiple-organ inflammation, injury and/or failure, which may be caused by internal or external trauma (e.g. injury), or by an infection.

Such conditions may thus result from sepsis or septic shock caused by a viral, bacterial or fungal infection. Furthermore, acute lung injury, ARDS and, particularly, SARS may be caused by viruses, such as coronaviruses, include SARS-COV-2, which may result in internal tissue damage and/or dysfunction of relevant internal (e.g. mucosal) tissues, and/or the cells that comprise them, such as the respiratory epithelium. Such tissue damage may in turn give rise to severe fibrosis. For example, the SARS disease caused by SARS-COV-2 (coronavirus disease 2019 or COVID-19) is known in many cases to result in fibrosis.

However, dosage forms of the invention are also espe-cially useful in the treatment or prevention of ILDs as defined herein, including sarcoidosis or fibrosis, more spe-cifically pulmonary fibrosis and particularly IPF, as well as conditions that may trigger ILDs, such as systemic sclerosis, rheumatoid arthritis, myositis or systemic lupus erythema-tosus, or are otherwise associated with ILDs, such as pul-monary hypertension and/or pulmonary arterial hyperten-sion.

The term 'ILD' will be understood by those skilled in the art to include any pulmonary condition characterized by an abnormal healing response, including chronic inflammation, reduced lung function and/or scarring, irrespective of the cause, such as sarcoidosis, and PF, especially IPF. The term may also include diseases and/or conditions that are known to lead to, and/or be causes of, such pulmonary conditions, such as systemic sclerosis. In this respect there is further provided a dosage form of the invention for use in the condition that leads to and/or is a cause of an ILD, such as PF or IPF, including systemic sclerosis.

In the treatment of PF, including IPF, dosage forms of the invention may have an anti-fibrotic effect, with reduction of fibrosis and prevention of further deposition of extra cellular matrix. Dosage forms of the invention may affect lung scarring/wound healing and also have an anti-apoptotic effect, thereby preventing apoptosis for alveolar endothelial cells, being an initiating factor for the development of PF. Dosage forms of the invention may also have an anti-proliferative effect, thus reducing the cancer-like prolifera-tion of fibroblasts and myofibroblasts in PF. Dosage forms of the invention may also improve vascular remodelling in PF, thereby reducing secondary pulmonary hypertension. Finally, dosage forms of the invention may demonstrate anti-inflammatory and anti-cytokine effects.

According to a further aspect of the present invention, there is provided a method of treatment of any of the aforementioned conditions, including respiratory viral dam-age and, more particularly, an ILD, including PF, and in particular IPF, which method comprises administration of a therapeutically effective amount of a dosage form of the invention to a person suffering from, or susceptible to, such a condition.

According to a yet further aspect of the present invention, there is provided a method of treatment of respiratory virus-induced tissue damage in a subject, which method comprises administration of a therapeutically effective amount of a dosage form of the invention to a subject in need of such treatment, particularly in which:

the tissue that is damaged is lung tissue, including the respiratory epithelium;

the damage comprises injury and/or dysfunction of the mucosal tissue of the respiratory tract caused by a respiratory virus;

the treatment includes treatment, and/or arresting the progress, of a disease that is being, or has been, caused by the virus;

the respiratory virus is a coronavirus, such as SARS-COV-2, and the disease is a SARS, such as COVID-19; or the respiratory virus is an influenza virus, and the disease is influenza;

the treatment includes treatment of the symptoms of the disease that is being, or has been, caused by the relevant virus;

the symptoms of the damage or the disease include one or more of cough, dyspnea, respiratory distress (which may be manifest by the need for supplementary oxygen and/or mechanical ventilation), respiratory failure, pneumonia, fibrosis in one or more internal organs, including the lungs, the heart and/or the kidneys; and/or the treatment includes prevention of respiratory virus-induced morbidity and/or mortality in one or more of the foregoing conditions.

The dosage forms of the invention are indicated both in the therapeutic, palliative, and/or diagnostic treatment (e.g. during diagnostic workup if a condition is suspected), as well as the prophylactic treatment (by which we include preventing and/or abrogating deterioration and/or worsening of a condition) of any of the above conditions.

'Patients' include avian and mammalian (particularly human) patients. Human patients include both adult patients as well as pediatric patients, the latter including patients up to about 24 months of age, patients between about 2 to about 12 years of age, and patients between about 12 to about 16 years of age. Patients older than about 16 years of age may be considered adults for purposes of the present invention. These different patient populations may be given different doses of C21 or salt thereof.

It is preferred, in the treatment of certain conditions such as respiratory virus-induced tissue damage, that C21 or a pharmaceutically-acceptable salt thereof is administered to adult patients, more particularly subjects that are over the age of about 20, such as over the age of about 30, including over the age of about 40, more preferably over the age of about 50, especially over the age of about 60, particularly over the age of about 70, and more particularly over the age of about 80 years of age; and/or to patients (whether or not such patients are in one of the age groups specified above) with one or more of the following underlying medical conditions:

chronic (long-term) respiratory diseases, such as pulmonary fibrosis, pulmonary hypertension, pulmonary arterial hypertension, other ILDs, asthma, chronic obstructive pulmonary disease (COPD), emphysema or bronchitis chronic cardiovascular (e.g. heart) disease, such as heart failure, atrial fibrillation or hypertension chronic kidney disease chronic liver disease, such as hepatitis chronic neurological conditions, such as Parkinson's disease, motor neurone disease, multiple sclerosis, a learning disability or cerebral palsy diabetes problems with a patient's spleen—for example, sickle cell disease or if the spleen has been removed a weakened immune system as the result of conditions, such as HIV and AIDS, or medicines such as steroid tablets or chemotherapy obesity (e.g. a body mass index (BMI) of 40 or above)

pregnancy.

In this respect, according to several further aspects of the invention there is provided a method of treatment and/or prevention of one or more the following conditions:

post-acute sequelae of e.g. SARS-COV-2 infection (PASC), such as what is known as 'long COVID', 'chronic COVID syndrome' (CCS) and/or 'long-haul COVID';

acute kidney injury and/or chronic kidney disease;

respiratory diseases such as pulmonary fibrosis, pulmonary hypertension, pulmonary arterial hypertension, asthma, chronic obstructive pulmonary disease (COPD), emphysema and/or bronchitis; and cardiovascular diseases such as myocardial infarction, heart failure, atrial fibrillation, hypertension or thrombosis and/or embolization in e.g. the heart, lungs and/or brain, all of which may be induced, directly or indirectly, by respiratory viruses (such as SARS-COV-2), which method comprises administering C21 or a pharmaceutically-acceptable salt thereof to a subject in need of such treatment and/or prevention.

In relation to (for example) acute treatment of respiratory virus-induced tissue damage, doses of C21 or salt thereof may be administered between once and four times (e.g. between 1 and 3 times) daily for up to three (e.g. two) months, such as one month, including up to three weeks, e.g. up to one week, such as 4 days or 3 days. Such treatment periods may be repeated as appropriate.

In the case of the development of one or more of the chronic symptoms identified hereinbefore, such as fibrosis of the lungs and other internal organs, treatment with C21 or salt thereof may, in addition to and/or instead of the above-mentioned acute dosing regimens, be continuous and/or as needed/required.

Relevant active ingredients that may be used in combination therapy with C21 in the treatment of patients with viral infections include more the variously-applied standard treatments for viral infections, including antibody therapies (e.g. LY-CoV555/LY-CoV016 (bamlanivimab and etesevimab), LY-CoV555 (bamlanivimab, Eli Lilly), REGN-COV2 (casirivimab and imdevimab), REGN3048-3051, TZLS-501, SNG001 (Synairgen), eculizumab (Soliris; Alexion Pharmaceuticals), ravulizumab (Ultomiris; Alexion Pharmaceuticals), lenzilumab, leronlimab, tocilizumab (Actemra; Roche), sarilumab (Kevzara; Regeneron Pharma), and Octagam (Octapharma)), antiviral medicines (e.g. oseltamivir, remdesivir, favilavir, molnupiravir, simeprevir, daclatasvir, sofosbuvir, ribavirin, umifenovir, lopinavir, ritonavir, lopinavir/ritonavir (Kaletra; AbbVie Deutschland GmbH Co. KG), teicoplanin, baricitinib (Olumiant; Eli Lilly), ruxolitinib (Jakavi; Novartis), tofacitinib (Xeljanz; Pfizer), the TMPRSS2 inhibitor, camostat, or camostat mesylate, Actembra (Roche), TZLS-501, AT-100 (rhSP-D), MK-7110 (CD24Fc; Merck)), OYA1 (OyaGen9), BPI-002 (Beyond-Spring), NP-120 (Ifenprodil; Algernon Pharmaceuticals), Galidesivir (Biocryst Pharma), antiinflammatory agents (e.g. NSAIDs, such as ibuprofen, ketorolac, naproxen and the like), chloroquine, hydroxychloroquine, interferons (e.g. interferon beta (interferon beta-1a), tocilizumab (Actemra), lenalidomide, pomalidomide and thalidomide), analgesics (e.g. paracetamol or opioids), antitussive agents (e.g. dextromethorphan), vaccinations (e.g. INO-4800 by Inovio Pharmaceuticals and Beijing Advaccine Biotechnology, if available), COVID-19 convalescent plasma (CCP) and/or passive antibody therapy with antibodies from blood of people who have recovered from infection with SARS-COV or SARS-COV-2.

Relevant active ingredients that may be used in combination therapy with C21 in the treatment of ILDs, such as IPF include, for example, anti-fibrotics, (e.g. nintedanib and, particularly, pirfenidone); vitamins (e.g. vitamin B, C and D); mucolytics (e.g. acetylcysteine and ambroxol); corticosteroids, such as cortisone and prednisone; inflammation suppressants, such as cyclophosphamide; other immunosuppressants, such as azathioprine and mycophenolate mofetil; and antioxidants, such as N-acetylcysteine. Relevant active ingredients that may be used in combination therapy with C21 in the treatment of sarcoidosis include, for example, corticosteroids, such as cortisone, prednisone and prednisolone; antimetabolites; immune system suppressants, such as methotrexate, azathioprine, leflunomide, mycophenoic acid/ mycophenolate mofetil, cyclophosphamide; aminoquinolines; monoclonal anti-tumor necrosis factor antibodies, such as infliximab and adalimumab; immunomodulatory imide drugs, such as include lenalidomide, pomalidomide and, especially, thalidomide; the TNF inhibitor, etanercept; and painkillers, such as ibuprofen and paracetamol; cough suppressants and/or expectorants.

For the avoidance of doubt, 'corticosteroids' as mentioned above include both naturally-occurring corticosteroids and synthetic corticosteroids.

Naturally-occurring corticosteroids that may be mentioned include cortisol (hydrocortisone), aldosterone, corticosterone, cortisone, pregnenolone, progesterone, as well as naturally-occurring precursors and intermediates in corticosteroid biosynthesis, and other derivatives of naturally-occurring corticosteroids, such as 11-deoxycortisol, 21-deoxycortisol, 11-dehydrocorticosterone, 11-deoxycorticosterone, 18-hydroxy-11-deoxycorticosterone, 18-hydroxycorticosterone, 21-deoxycortisone, 11β-hydroxypregnenolone, 11β,17α,21-trihydroxypregnenolone, 17α,21-dihydroxypregnenolone, 17α-hydroxypregnenolone, 21-hydroxypregnenolone, 11-ketoprogesterone, 11β-hydroxyprogesterone, 17α-hydroxyprogesterone and 18-hydroxyprogesterone.

Synthetic corticosteroids that may be mentioned include those of the hydrocortisone-type (Group A), such as cortisone acetate, hydrocortisone aceponate, hydrocortisone acetate, hydrocortisone buteprate, hydrocortisone butyrate, hydrocortisone valerate, tixocortol and tixocortol pivalate, prednisolone, methylprednisolone, prednisone, chloroprednisone, cloprednol, difluprednate, fluperolone, fludrocortisone, fluocinolone, fluprednisolone, loteprednol, prednicarbate and triamcinolone; acetonides and related substances (Group B), such as amcinonide, budesonide, desonide, fluocinolone cetonide, fluocinonide, halcinonide, triamcinolone acetonide, ciclesonide, deflazacort, formocortal, fludroxycortide, flunisolide and fluocinolone acetonide, those of the (beta)methasone-type (Group C), such as beclomethasone, betamethasone, betamethasone dipropionate and betamethasone valerate, dexamethasone, fluocortolone, halometasone, mometasone and mometasone furoate, alclometasone and alclometasone dipropionate, clobetasol and clobetasol propionate, clobetasone and clobetasone butyrate, clocortolone, desoximetasone, diflorasone, difluocortolone, fluclorolone, flumetasone, fluocortin, fluprednidene and fluprednidene acetate, fluticasone, fluticasone furoate and fluticasone propionate, meprednisone, paramethasone, prednylidene, rimexolone and ulobetasol; those of the progesterone-type, such as flugestone, fluorometholone, medrysone and prebediolone acetate, and progesterone derivatives (progestins), such as chlormadinone acetate, cyproterone acetate, medrogestone, medroxyprogesterone acetate, megestrol acetate and segesterone acetate; as well as other corticosteroids, such as cortivazol and 6-methyl-11β, 17β-dihydroxy-17α-(1-propynyl)androsta-1,4,6-trien-3-one.

Preferred corticosteroids include cortisone, prednisone, prednisolone, methylprednisolone and, especially, dexamethasone.

Further, relevant active ingredients that may be used in combination therapy with C21 (e.g. to treat respiratory viral infections) include H2 receptor blockers, anticoagulants, anti-platelet drugs, as well as statins, antimicrobial agents and anti-allergic/anti-asthmatic drugs.

H2 receptor blockers that may be mentioned include famotidine. Anticoagulants that may be mentioned include heparin and low-molecular-weight heparins (e.g. bemiparin, nadroparin, reviparin, enoxaparin, parnaparin, certoparin, dalteparin, tinzaparin); directly acting oral anticoagulants (e.g. dabigatran, argatroban, rivaroxaban, apixaban, edoxaban, betrixaban, darexaban, otamixaban, letaxaban, eribaxaban, hirudin, lepirudin and bivalirudin); coumarin type vitamin K antagonists (e.g. coumarin, acenocoumarol, phenprocoumon, atromentin and phenindione) and synthetic pentasaccharide inhibitors of factor Xa (e.g. fondaparinux, idraparinux and idrabiotaparinux). Anti-platelet drugs that may be mentioned include irreversible cyclooxygenase inhibitors (e.g. aspirin and triflusal); adenosine diphosphate receptor inhibitors (e.g. cangrelor, clopidogrel, prasugrel, ticagrelor and ticlopidine); phosphodiesterase inhibitors (e.g. cilostazol); protease-activated receptor-1 antagonists (e.g. vorapaxar); glycoprotein IIB/IIIA inhibitors (e.g. abciximab, eptifibatide and tirofiban); adenosine reuptake inhibitors (e.g. dipyridamole); and thromboxane inhibitors (e.g. terutroban, ramatroban, seratrodast and picotamide). Statins that may be mentioned include atorvastatin, simvastatin and rosuvastatin. Antimicrobial agents that may be mentioned include azithromycin, ceftriaxone, cefuroxime, doxycycline, fluconazole, piperacillin, tazobactam and teicoplanin. Anti-allergic/anti-asthmatic drugs that may be mentioned include chlorphenamine, levocetirizine and montelukast.

Further relevant active ingredients that may be used in combination therapy with C21 (e.g. to treat respiratory viral infections) include other AT2 agonists that are known in the art as well as in combination with AT1 receptor antagonists that are known in the art, and/or in combination with an inhibitor of angiotensin converting enzyme (ACE). Non-limiting but illustrative examples of AT1 receptor antagonists that can be used according to the embodiments include azilsartan, candesartan, eprosartan, fimasartan, irbesartan, losartan, milfasartan, olmesartan, pomisartan, pratosartan, ripiasartan, saprisartan, tasosartan, telmisartan, valsartan and/or combinations thereof. Non-limiting but illustrative examples of ACE inhibitors that can be used according to the embodiments include captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and/or combinations thereof.

Relevant patients may also (and/or may already) be receiving one or more of any of the treatments and/or other therapeutic agents mentioned above for the relevant condition based upon administration of one or more of such active ingredients, by which we mean receiving a prescribed dose of one or more of those active ingredients mentioned herein, prior to, in addition to, and/or following, treatment with C21 or a salt thereof.

Pharmaceutically-acceptable salts, and doses, of other active ingredients mentioned above include those that are known in the art and described for the drugs in question to in the medical literature, such as Martindale—The Complete Drug Reference, 38th Edition, Pharmaceutical Press, London (2014) and the documents referred to therein, the relevant disclosures in all of which documents are hereby incorporated by reference.

Dosage forms of the invention have the advantage that they can be manufactured and stored under normal storage conditions, including without freezing and/or being exposed to light, maintaining pharmaceutically-acceptable physico-chemical stability of the composition contained with the capsule and, in particular, the active ingredient.

Dosage forms of the invention may also provide for an improved drug loading, enable high quantities/doses of active compound to be presented, and also efficient delivery of such higher doses in a consistent/uniform manner. This in turn enhances the effectiveness and efficiency of treatment and reduces costs for healthcare.

The uses/methods described herein may otherwise have the advantage that, in the treatment of one or more of the conditions mentioned hereinbefore, and in particularly ILDs and/or respiratory viral infections, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art, whether used in those conditions or otherwise.

Wherever the word 'about' is employed herein, for example in the context of numbers or amounts, i.e. absolute amounts such as sizes (e.g. particle sizes), doses, weights or concentrations of (e.g. active) ingredients, ages, temperatures or time periods; or relative amounts including percentages and standard deviations, it will be appreciated that such variables are approximate and as such may vary by ±10%, for example ±5% and preferably ±2% (e.g. ±1%) from the actual numbers specified. In this respect, the term 'about 10%' means e.g. ±10% about the number 10, i.e. between 9% and 11%.

The invention is illustrated, but in no way limited, by the following examples.

EXAMPLES

Comparative Example 1—Solubility of C21 in Water

The solubility of free C21 was investigated in a number of different aqueous vehicles as summarised in Table 1 below.

Vehicles (with sources) were as follows: sodium chloride (Sigma), ethanol (99.5%, Kemetyl), polyethylene glycols (BASF), phosphate buffered saline (PBS) pH 7.4 (Sigma), buffer solution pH 2.00 (citric acid, sodium hydroxide, hydrogen chloride), buffer solution pH 4.00 (citric acid, sodium hydroxide), buffer solution pH 6.00 (citric acid, sodium hydroxide), buffer solution pH 8.00 (boric acid, sodium hydroxide, hydrogen chloride) and buffer solution pH 10.00 (boric acid, sodium hydroxide, hydrogen chloride) (all Merck), and purified water (Elga Option 4 water purifier).

Saturated solutions of free C21 (obtained from Syntagon AB, Södertälje, Sweden) were prepared in duplicates. The samples were kept magnetically stirred for 48 hours prior to analysis. For some samples, the added substance was dissolved and more was thereafter added to obtain saturated solutions.

After 48 hours, pH was measured and thereafter 1 mL of solution was withdrawn. Undissolved substance was removed by centrifugation (1500 rpm, 30 minutes). The supernatant was diluted 10 to 500 times with acetonitrile/$H_2O$, 30:70.

C21 content was measured by HPLC.

TABLE 1

| Vehicle | Concentration (mg/mL)[a] | pH |
|---|---|---|
| $H_2O$ | 0.15 | 7.3 |
| 0.9% NaCl | 0.12 | 7.3 |
| 0.9% NaCl | 1.58[b] | 8.3[c] |
| 0.9% NaCl | 27.40 | 9.7[c] |
| 0.9% NaCl/EtOH 95:5 v/v | 0.57[b] | 7.9 |
| Buffer/Citric acid pH 2.0 | 3.95 | 2.3 |
| Buffer/Citric acid pH 4.0 | 0.08 | 4.0 |

TABLE 1-continued

| Vehicle | Concentration (mg/mL)[a] | pH |
|---|---|---|
| Buffer/Citric acid pH 6.0 | 0.06 | 6.0 |
| Buffer/PBS pH 7.4 | 0.24 | 7.7 |
| Buffer/Boric acid pH 8.0 | 0.50 | 7.9 |
| Buffer/Boric acid pH 10.0 | 19.10, 19.90 | 8.7 |
| PEG/$H_2O$ (25:75) | 0.17 | 5.5 |
| PEG/$H_2O$ (50:50) | 0.61 | 6.2 |
| PG/$H_2O$ (10:90) | 0.22 | 7.5 |
| PG/$H_2O$ (25:75) | 0.30 | 6.9 |
| PEG/EtOH/$H_2O$ (40:10:50) | 0.83 | 6.1 |
| PG/EtOH/$H_2O$ (40:10:50) | 0.79 | 6.3 |

[a]Concentrations are mean values from two separate samples
[b]Concentrations are mean values from two injections (one sample)
[c]pH was adjusted by addition of NaOH Above pHs of approximately 8.5, there is a marked increase in free C21 solubility. As much as 27.4 mg/ml is obtained at pH 9.7 in a 0.9% NaCl solution.

An increased solubility is also seen in the co-solvent systems studied. The change is however not as dramatic as by modification of pH.

The solubility of the sodium salt of C21 was measured by way of a similar experiment and was found to be considerably higher than free C21.

In this experiment, C21 sodium salt (Syntagon AB) was added to the vehicle, small amounts at a time. About 20-30 mg of the sodium salt was easily dissolved in all the vehicles tested. Salt was continuously added to the same sample in an attempt to obtain a saturated solution. In this way, higher amounts, such as 40-60 mg/mL could be dissolved. The solubility is probably even higher than this in the vehicles tested, but this was not established in view of the limited amount of drug compound available. The results are summarised in Table 2 below.

TABLE 2

| Vehicle | Concentration (mg/mL)[a] | pH |
|---|---|---|
| $H_2O$ | >65 | 9.8 |
| 0.9% NaCl | >40 | 9.3 |
| PBS pH 7.4 | >40 | 9.4 |

[a]Concentrations are mean values from two separate samples

Comparative Example 2-Sensitivity of Aqueous Solutions of C21 to Light

The stability of free C21 in 0.9% NaCl pH 9.4 was investigated.

Solutions of 1 mg/ml of C21 were studied for four weeks under four different storage conditions. The solution was filtered through a 0.22 sterile syringe filter to minimize bacterial growth during the stability test. The samples were analysed by HPLC for purity.

The results are summarised in Table 3 below, in which the amount of C21 is given as a percentage of the initial amount of drug. Solution pHs were also measured and are shown within parenthesis in Table 3.

21

TABLE 3

| Storage time (weeks) | Amount of Free C21, % of initial | | | |
|---|---|---|---|---|
| | 5° C., dark | RT, dark | RT, light | 40° C., dark |
| Initial[a] | 100 (9.4) | 100 (9.4) | 100 (9.4) | 100 (9.4) |
| 1[a] | 101 (9.2) | 97 (9.2) | 96 (9.0) | 101 (9.0) |
| 2[b] | 107 (9.2) | 109 (8.9) | 44 (8.0) | 111 (8.6) |
| 3[b] | 108 (9.1) | 105 (9.0) | 96 (8.5) | 106 (8.7) |
| 4[b] | 108 (9.2) | 106 (8.9) | 13 (7.7) | 107 (8.7) |

[a]Analyst A
[b]Analyst B

Free C21 was found to be chemically stable when stored in dark at 5° C., room temperature (RT) and at 40° C. for four weeks. There appears to be a slight decrease in pH when the solution is stored at room temperature or above, but not when it is stored cold.

Peaks in the HPLC chromatogram that correspond to impurities/degradation products were followed by their respective peak area. The total impurity peak area was around 2.5 area % of C21 peak area for the samples stored at 5° C., RT/dark and 40° C.

There is a clear increase in number of impurity peaks in the samples stored at RT/light which suggests that the substance is chemically degraded when exposed to light (at least in the presence of water). Especially, a peak at relative retention time of 0.84 correspond to 6.9 minutes appears under this storage condition.

Precipitation was observed in the sample stored for two and four weeks in RT/light and the samples were therefore filtered (0.45 μm, GHP/Acrodisc) prior to analysis. The comparably low content of 44% and 13%, respectively, may be due to precipitation of C21 which may occur at pHs below 8.0. It is however clear that the decrease in content is also due to formation of degradation products at this storage condition. A number of other impurity peaks were observed by HPLC, which are likely related to the degradation of C21 under this storage condition.

A possible explanation of the pH drop in the sample stored for several weeks in RT/light is that degradation of the substance causes a decrease in pH which in turn sets a limit to the solubility of C21 itself.

The stability of the sodium salt of C21 was also investigated under the same storage conditions. The results are summarised in Table 4 below.

TABLE 4

| Storage time (weeks) | Amount of Free C21, % of initial | | | |
|---|---|---|---|---|
| | 5° C., dark | RT, dark | RT, light | 40° C., dark |
| Initial[a] | 100 (8.3) | 100 (8.3) | 100 (8.3) | 100 (8.3) |
| 1[a] | 108 (8.5) | 115 (8.6) | 108 (8.4) | 111 (8.6) |
| 2[b] | 113 (8.4) | 110 (8.8) | 96 (8.0) | 111 (8.5) |
| 3[b] | 113 (8.5) | 111 (8.8) | 72 (8.3) | 109 (8.7) |
| 4[b] | 112 (8.5) | 112 (8.2) | 9 (7.3) | 118 (8.1) |

[a]Analyst A
[b]Analyst B

At the time for analysis of the one week samples, it was noted that the heating cabinet for storage of samples at 40° C. was broken. In view of this, these samples were thereafter kept at room temperature for three days.

As with free C21, the sodium salt is chemically stable after 4 weeks when kept in the dark at all temperatures studied. For the samples stored at RT/light there is a peak occurring at the same relative retention time as observed for free C21. There are also a number of other peaks, which it was thought were related to light induced degradation.

The conclusion is therefore that light-induced degradation occurs in both the sodium salt and free C21.

This presented a significant challenge for development of C21. For any future pharmaceutical product, it is difficult to ensure the complete avoidance of ambient temperatures (or higher), light and moisture at the same time, during drug manufacture, formulation manufacture, packaging, transportation and storage.

It was subsequently decided to formulate C21 as the sodium salt in an aqueous solution in the presence of a carbonate buffer for oral dosing, at concentrations of 0.2 and 10 mg/mL for further pre-clinical and clinical development. Such frozen formulations were found to be chemically stable for 3 months when stored refrigerated in polyethylene terephthalate (PET) bottles and for 36 months when stored in a freezer at −15° C., with no degradation changes in pH or appearance or assay having been observed.

Comparative Example 3—Attempts to Make Dry Blends

Two simple blend capsule formulations comprising C21 sodium salt (obtained from Syntagon AB, Södertälje, Sweden) were manufactured by Turbula mixing for 20 minutes at 67 rpm. Ten capsules were filled with each of the simple blends which has the compositions presented in Table 5 below. The capsules of each batch were divided into three groups; stored in a freezer, at room temperature and at 40° C. for 6 weeks.

TABLE 5

| Ingredient | Amount/Capsule (nominal in mg) | |
|---|---|---|
| | Batch 1 | Batch 2 |
| C21 as Na-salt | 25 | 25 |
| D-Mannitol | 264 | — |
| Sodium Starch Glycolate | 31 | — |
| MCC, Pharmacel 102 | — | 226 |
| Croscarmellose Sodium | — | 16 |
| Hard Gelatin Capsule | 96 | 96 |
| Nominal weight/capsule | 388 | 363 |

(Sources: D-mannitol (Sigma Aldrich); sodium starch glycolate (Glycolys ®; Roquette); microcrystalline cellulose (MCC, Pharmacel ® 102, DFE Pharma); croscarmellose sodium (Vivasol ®; JRS Pharma) and hard gelatin capsule (Licaps ® Gel T0 Orange, Capsugel).)

Three capsules from each batch and storage condition were analysed after 6 weeks. The results of assay, homogeneity and related impurities are presented in Tables 6 (Batch 1) and 7 (Batch 2) below.

TABLE 6

| Storage condition | Capsule No | C21 parent found of label claim (%) | Impurities (Area-%) | | |
|---|---|---|---|---|---|
| | | | 1 | 2 | Sum (≥0.05) |
| Freezer/6 weeks | 1 | 97 | 0.23 | 0.02 | 0.23 |
| | 2 | 98 | 0.23 | 0.02 | 0.23 |
| | 3 | 106 | 0.25 | 0.02 | 0.25 |
| | Average | 100 | 0.24 | 0.02 | 0.24 |
| | % RSD | 4.9 | | | |
| RT/6 weeks | 1 | 95 | 0.25 | 0.04 | 0.25 |
| | 2 | 106 | 0.25 | 0.04 | 0.25 |
| | 3 | 92 | 0.24 | 0.04 | 0.24 |
| | Average | 98 | 0.25 | 0.04 | 0.25 |
| | % RSD | 7.5 | | | |

TABLE 6-continued

| Storage condition | Capsule No | C21 parent found of label claim (%) | Impurities (Area-%) | | |
|---|---|---|---|---|---|
| | | | 1 | 2 | Sum (≥0.05) |
| 40° C./6 weeks | 1 | 94 | 0.34 | 0.15 | 0.49 |
| | 2 | 91 | 0.33 | 0.16 | 0.48 |
| | 3 | 101 | 0.32 | 0.14 | 0.47 |
| | Average | 95 | 0.33 | 0.15 | 0.48 |
| | % RSD | 5.4 | | | |

TABLE 7

| Storage condition | Capsule No | C21 parent found of label claim (%) | Impurities (area-%) | | |
|---|---|---|---|---|---|
| | | | 1 | 2 | Sum (≥0.05) |
| Freezer/6 weeks | 1 | 105 | 0.25 | 0.03 | 0.25 |
| | 2 | 112 | 0.25 | 0.02 | 0.25 |
| | 3 | 97 | 0.25 | 0.03 | 0.25 |
| | average | 105 | 0.25 | 0.03 | 0.25 |
| | % RSD | 7.0 | | | |
| RT/6 weeks | 1 | 90 | 0.28 | 0.02 | 0.28 |
| | 2 | 95 | 0.28 | 0.03 | 0.28 |
| | 3 | 97 | N/A* | N/A* | N/A* |
| | average | 94 | 0.28 | 0.03 | 0.28 |
| | % RSD | 3.8 | | | |
| 40° C./6 weeks | 1 | 96 | 0.53 | 0.03 | 0.53 |
| | 2 | 91 | 0.54 | 0.03 | 0.54 |
| | 3 | 90 | 0.55 | 0.03 | 0.55 |
| | average | 92 | 0.54 | 0.03 | 0.54 |
| | % RSD | 3.6 | | | |

*Excluded for impurity determinations since the specific syringe filter used for this sample gives adsorption of Impurity 1 (previously known for C21).

For each of the batches, the average assay at storage condition freezer was found to be close to 100%. For both batches, the assay decreased in the following order: freezer, RT, 40° C. Additionally, the total sum of organic impurities increases in the same order for both batches.

A notable variability in assay results was seen within each set of capsules. In Batch 1, the total sum of impurities was 0.24 area % units higher for storage at 40° C. compared to the freezer. Novel Impurity 2 constituted the major increase, from 0.02 to 0.15 area %. The known Impurity 1 increased by 0.09 area % units. Two further impurity peaks just below the reporting limit 0.05 area % were also formed.

In Batch 2, the total sum of impurities was 0.29 area % units higher for storage at 40° C. compared to the freezer. This increase is solely due to an increase of Impurity 1.

Three capsules of each batch stored at ambient room temperature were analysed with regards to dissolution. Batch 1 was fully released at 15 minutes, with a low variability in data. For Batch 2, two out of three capsules were fully released at 30 minutes, but there was a large variability in results.

The degradation of C21 in the two early simple blend capsule formulations seen during the stability testing was considered unacceptably high. Chemical stability of the C21 capsule formulation became the main focus in the continued development work. Also, it was concluded that further work could become necessary in order to achieve a homogeneous powder blend.

Comparative Example 4—Compatibility Study

The excipients used in the capsules in Comparative Example 3 above were evaluated along with some additional ones (see Table 8 below).

C21 (sodium salt) used in these experiments was ground and passed through a 300 μm sieve. Mixtures of each excipient and C21 were prepared by thorough mixing in the amounts specified in Table 8. The ratio of C21 to various fillers (D-mannitol, MCC, lactose monohydrate and HPMC) was adapted to give a volume equivalent to the larger part of a capsule.

Three capsules of each type were filled with C21. All preparations were stored under accelerated stability conditions at 60° C. for 12 days prior to analysis.

TABLE 8

| Chemical | Sample Number | | | | | | | | | |
|---|---|---|---|---|---|---|---|---|---|---|
| | 1 | 2 | 3 | 4 | 5 | 6 | 7 | 8 | 9 | 10 |
| C21 (mg) | 26 | 26 | 25 | 25 | 24 | 26 | 25 | 25 | 25 | 25 |
| D-Mannitol (mg) | 464 | — | — | — | — | — | — | — | — | — |
| Sodium Starch Glycolate (mg) | — | 35 | — | — | — | — | — | — | — | — |
| MCC, Pharmacel 102 (mg) | — | — | 229 | — | — | — | — | — | — | — |
| Croscarmellose Sodium (mg) | — | — | — | 17 | — | — | — | — | — | — |
| Hard Gelatin Capsule | — | — | — | — | 3 pcs | — | — | — | — | — |
| MCC, Vivapur 102 (mg) | — | — | — | — | — | 229 | — | — | — | — |
| Lactose mono-hydrate (mg) | — | — | — | — | — | — | 249 | — | — | — |
| HPMC Methocel (mg) | — | — | — | — | — | — | — | 259 | — | — |
| HPMC Capsule | — | — | — | — | — | — | — | — | 3 pcs | — |

(Sources of different materials to those tested above: MCC (Vivapur ® 102, JRS Pharma); lactose monohydrate (InhaLac ® 400, Meggle); hydroxypropyl methylcellulose (HPMC, Methocel ™ K100 Premium, Colorcon); and HPMC capsules (Licaps ® size 0; Capsugel).)

The results of the related impurity analysis after 12 days at 60° C. are presented in Table 9 below and FIG. 1.

TABLE 9

| Sample No. | Chemical | Degradation | | | | | |
|---|---|---|---|---|---|---|---|
| | | Sum of impurities (≥0.05%) | Individual Impurity (area %) | | | | |
| | | | 1 | 2 | 3 | 4 | 5 |
| 1 | D-Mannitol | 0.26 | 0.26 | | | | |
| 2 | Sodium Starch Glycolate | 0.73 | 0.53 | 0.20 | | | |
| 3 | MCC Pharmacel 102 | 11.1 | 11.0 | | | | 0.0 |
| 4 | Croscarmellose Sodium | 0.52 | 0.52 | | | | |
| 5 | Licaps hard gelatin capsule | 0.28 | 0.28 | | | | |
| 6 | MCC Vivapur 102 | 0.56 | 0.56 | | | | |
| 7 | Lactose monohydrate | 0.48 | 0.40 | | | 0.08 | |
| 8 | HPMC Methocel | 1.74 | 1.74 | | | | |
| 9 | Licaps HPMC capsule | 0.35 | 0.30 | | 0.05 | | |
| 10 REF | C21 only | 0.26 | 0.26 | | | | |

No degradation of C21 was observed in Sample Nos. 1 and 5 in the accelerated stability study, nor in the reference sample. In Sample No. 3, a very large degradation of C21 to Impurity 1 took place, and in Sample No. 8 showed a similar degradation. All other mixtures showed degradation of C21 and, in some mixtures, new degradation products were formed besides the known Impurity 1.

In addition to the disintegrants (sodium starch glycolate and croscarmellose sodium) mentioned above, crospovidone of two different types (Kollidon® CL (Type A), and Kollidon® CL-SF (Type B) (both BASF) were tested.

Mixtures of 130 mg crospovidone and 200 mg C21 were prepared and were thoroughly mixed using a Turbula mixer for 10 minutes. All of these preparations were analysed at time zero and after storage at accelerated stability conditions at 60° C. for 12 days.

The results of the related impurity analyses for the study run at 60° C. are presented in Table 10 below. No significant degradation of C21 was observed in any of the mixtures. The impurity peaks number 6 and 7 observed using Kollidon CL were present at the start.

TABLE 10

| Tested Kollidon | Timepoint (days) | Sum of impurities (≥0.05%) | Individual Impurity (area %) 1 | 6 | 7 |
|---|---|---|---|---|---|
| CL, Type A | 0 | 0.26 | 0.26 | 0.01 | 0.01 |
| | 12 | 0.28 | 0.28 | 0.01 | 0.01 |
| CL-SF, Type B | 0 | 0.25 | 0.25 | n.d.[1] | n.d.[1] |
| | 12 | 0.25 | 0.25 | n.d.[1] | n.d.[1] |

[1]The peak is <0.003 area-%

The compatibility test shows that C21 is stable together with mannitol, both types of Kollidon, CL and CL-SF, and the Licaps hard gelatin capsules, but that there are various stability issues with all other tested excipients.

Comparative Example 5—Mixing Studies

The ability to produce homogeneous powder mixtures of C21 sodium salt was a significant concern after the early simple blend capsule formulation experiments (see Comparative Example 3 above).

Mannitol of different grades to that mentioned in Comparative Examples 3 and 4 above were chosen for further studies with a view to determining appropriate mixing parameters and to provide a chemically stable and homogeneous powder mixture that could be filled into capsules.

C21 sodium salt was used together with 7 different types of mannitol from two different manufacturers.

C21 and mannitol were added to glass flasks and were mixed together using a Turbula mixer. At a mixing time of 30 minutes, each flask was sampled for homogeneity and related impurities were analysed.

An aliquot of each powder mixture was also subjected to 60° C. for 12 days in a stability analysis. The nominal content of C21 was 7.4% w/w (calculated as free C21) for all mannitol mixtures except one, where an additional strength of 14.8% w/w was also tested.

The results are presented in Table 11 below.

TABLE 11

| Mannitol | Sample preparation | C21 found of label claim (%) |
|---|---|---|
| Mannogem EZ Spray dried | 1 | 98.9 |
| | 2 | 101.8 |
| | 3 | 99.2 |
| | Mean value | 99.9 |
| | % RSD | 1.6 |

TABLE 11-continued

| Mannitol | Sample preparation | C21 found of label claim (%) |
|---|---|---|
| Mannogem EZ Spray dried | 1 | 95.3 |
| (with C21 14.8% w/w) | 2 | 104.1 |
| | 3 | 89.3 |
| | Mean value | 96.2 |
| | % RSD | 7.7 |
| Mannogem Granular | 1 | 66.5 |
| | 2 | 71.7 |
| | 3 | 67.6 |
| | Mean value | 68.6 |
| | % RSD | 4.0 |
| Mannogem 2080 Granular | 1 | 78.5 |
| | 2 | 108.3 |
| | 3 | 93.6 |
| | Mean value | 93.5 |
| | % RSD | 16 |
| Pearlitol 100 SD | 1 | 99.7 |
| | 2 | 88.7 |
| | 3 | 153.2 |
| | Mean value | 114 |
| | % RSD | 30 |
| Pearlitol 200 SD | 1 | 101.3 |
| | 2 | 132.6 |
| | 3 | 126.0 |
| | Mean value | 120 |
| | % RSD | 14 |
| Pearlitol 300 DC | 1 | 59.6 |
| | 2 | 73.9 |
| | 3 | 75.9 |
| | Mean value | 70 |
| | % RSD | 13 |
| Pearlitol 500 DC | 1 | 70.2 |
| | 2 | 66.5 |
| | 3 | 64.0 |
| | Mean value | 67 |
| | % RSD | 4.6 |

(Sources: all Mannogem ® types (SPI Pharma) and all Pearlitol ® types (Roquette).)

An acceptable homogeneity was only observed for both strengths of the Mannogem EZ Spray dried mannitol (mean particle size diameter 150 to 200 μm).

A variability in data points was however observed, which, whilst reasonable for the 7.4% strength was much higher for the 14.8% strength. All other mannitol types gave insufficient homogeneity and a high or very high variability. In this respect, it was noted that in the flasks where Mannogem Granular, Pearlitol 300 DC and Pearlitol 500 DC were mixed, part of the material adhered strongly to the glass walls. Based on the low amount of C21 found, it is believed that a higher amount of API was present in that sticky material.

The results of the accelerated stability study run at 60° C. for 12 days are presented in Table 12 below.

TABLE 12

| Chemical and type | Impurities ≥0.05% Formed (area %) 1 | 2 | 3 | 8 | 9 |
|---|---|---|---|---|---|
| C21 only, reference value | 0.26 | — | — | — | — |
| Mannitol Mannogem EZ Spray dried reference (no C21) | — | — | — | — | — |
| Mannitol Mannogem EZ Spray dried | 0.26 | — | — | 0.01 | 0.01 |
| Mannitol Mannogem EZ Spray dried 14.8% C21 | 0.26 | 0.01 | 0.02 | 0.01 | 0.01 |
| Mannitol Mannogem Granular | 0.27 | 0.01 | 0.02 | 0.01 | 0.01 |
| Mannitol Mannogem 2080 Granular | 0.27 | — | — | 0.01 | 0.01 |
| Mannitol Pearlitol 100 SD | 0.29 | 0.01 | 0.02 | 0.04 | 0.04 |
| Mannitol Pearlitol 200 SD | 0.26 | —** | —** | 0.01 | 0.02 |

TABLE 12-continued

| Chemical and type | Impurities ≥0.05% Formed (area %) | | | | |
|---|---|---|---|---|---|
| | 1 | 2 | 3 | 8 | 9 |
| Mannitol Pearlitol 300 DC | 0.28 | — | 0.02 | 0.03 | 0.04 |
| Mannitol Pearlitol 500 DC | 0.29 | 0.02 | 0.06 | 0.03 | 0.04 |
| Crospovidone Kollidon CL | 0.28 | 0.01* | 0.01* | — | — |
| Crospovidone Kollidon CL-SF | 0.25 | — | — | — | — |

*Observed at this level at T = 0 already
**Both were at the level 0.01 area-% at T = 0

C21 was found to be fairly stable towards all types of mannitol, though two new impurities were formed for all tested types (numbered 8 and 9 above). It has been shown in an 8 day accelerated stability study at 60° C. that these 2 impurities were not degradation products of mannitol. In any event, the levels of these impurities were low.

Two other impurities were detected earlier in the mixing experiments with Kollidon (see Comparative Example 4 above). The impurities were suspected to be non-homogeneously distributed degradation products of C21.

The impurities seemed to come and go, which is not an easily explainable behaviour. The known Impurity 1 showed a minor increase.

Comparative Example 6—Scaled-Up Mixing Studies

C21 and mannitol Mannogem EZ spray dried were added in glass flasks and mixed on a Turbula mixer. The nominal content of C21 was 7.78% w/w (calculated as free C21).

After mixing times 15, 30, 45, 60 and 90 minutes, the flask was sampled for homogeneity analyses. After the last sample was taken at 90 minutes, the remainder of the batch was passed through a 300 μm sieve, placed into a glass flask and then mixed further a Turbula mixer for 30 minutes before sampling. The results are presented in Table 13 below.

TABLE 13

| Mixing time (min) | Sample preparation | C21 found of label claim (%) |
|---|---|---|
| 15 | 1 | 103.3 |
| | 2 | 89.7 |
| | 3 | 95.3 |
| | 4 | 91.9 |
| | 5 | 100.8 |
| | Mean value | 96.2 |
| | % RSD | 6.0 |
| 30 | 1 | 99.5 |
| | 2 | 102.4 |
| | 3 | 99.5 |
| | 4 | 97.4 |
| | 5 | 109.7 |
| | Mean value | 101.7 |
| | % RSD | 4.7 |
| 45 | 1 | 102.9 |
| | 2 | 105.6 |
| | 3 | 102.9 |
| | 4 | 105.3 |
| | 5 | 96.3 |
| | Mean value | 102.6 |
| | % RSD | 3.7 |
| 60 | 1 | 103.1 |
| | 2 | 108.8 |
| | 3 | 94.2 |
| | 4 | 110.9 |
| | 5 | 100.0 |
| | Mean value | 103.4 |
| | % RSD | 6.5 |

TABLE 13-continued

| Mixing time (min) | Sample preparation | C21 found of label claim (%) |
|---|---|---|
| 90 | 1 | 96.6 |
| | 2 | 104.8 |
| | 3 | 103.1 |
| | 4 | 103.1 |
| | 5 | 100.4 |
| | Mean value | 101.6 |
| | % RSD | 3.1 |
| 90 + sieving and mixing | 1 | 87.7 |
| | 2 | 89.2 |
| | 3 | 89.1 |
| | 4 | 88.7 |
| | 5 | 88.7 |
| | Mean value | 88.7 |
| | % RSD | 0.67 |

The mean value for assay of C21 is close to 100% when a mixing time of 30 minutes or more is used compared to a mixing time of 15 minutes. There is, however, a large degree of variability (3-7% RSD) in the assay at each mixing time up to 90 minutes. Further, paradoxically, the homogeneity did not improve as a function of mixing time. The good homogeneity found for Mannogem EZ spray dried during screening of different types of mannitol (see Comparative Example 5 above) could thus not be repeated.

The final sieving and mixing gave a homogeneous mixture, 0.7% RSD, but the assay of C21 decreases substantially from 102 to 89%. This decrease is most likely due to the particle size distribution of C21 containing more aggregates of size of 100 to 400 μm.

Comparative Example 7—Mixing Following Micronization

A decision was then taken to try to micronize C21 prior to continuing the mixing experiments with mannitol.

An aliquot of C21 was sent to Jetpharma (Balerna, Switzerland) for micronization by jet-milling with a view to breaking up the aggregates of a particles size of 100 to 400 μm with a view to making a homogeneous mixture with mannitol.

It was found that the chemical purity of C21 did not change significantly during the micronization and the particle size distribution for the crystals in the material became narrower.

Light microscopy of the jet-milled C21 showed that the crystals were rod-shaped with lengths of a few μm up to 50 μm. The crystals were attracted to each other, forming loose clusters.

The micronized C21 and mannitol, Mannogem EZ Spray dried, were mixed in a similar manner to that described in Comparative Example 6 above. Again, although the mean value for C21 assay was close to 100% when a mixing time of 45 minutes or more was used, there was a large variability (4 to 10% RSD) in assay at each mixing time.

Further, again, the final sieving and mixing gave a homogeneous mixture, 0.7% RSD, but the assay of C21 decreased substantially from 103 to 88%. This decrease is of the same magnitude as the loss observed in Comparative Example 6 above for non-micronized C21.

Comparative Example 8—Mixing Using a Glidant

During the mixing experiments, it was observed that some of the powder mixture strongly adhered to the walls of the glass flask.

Thus, irrespective of how uniform the particle size was prior to mixing, the results strongly indicated that C21 has a propensity to form aggregates.

It was attempted to resolve this issue by adding colloidal silica. Both non-micronized and micronized C21 (see Comparative Example 7 above) were used and were mixed together with mannitol (Mannogem EZ spray dried) and Aerosil 200 colloidal silica.

C21 was pre-mixed along with colloidal silica (Aerosil® 200 Pharma, Evonik Industries) in a glass flask for 10 minutes using a Turbula mixer before mannitol was added with continued mixing. The same mixing and sampling procedure as that described above was employed.

During mixing, lumps were observed, which decreased in number with a longer mixing time. The mannitol itself contained, from the start, readily disintegrating lumps. At the mixing time of 30 minutes, one single lump of the mass 36 mg (constituting about 1/10 of the amount in a capsule) was isolated and analysed.

The content of C21 in that lump was only 24% of nominal content, which indicated that mannitol may need to be sieved before mixing with C21.

In the homogeneity analysis, the mean value for assay of C21 is initially very high (205%), but went down to around 100% at a mixing time of 30 minutes and longer. The variability decreases steadily with increasing mixing time but is at best 6% (i.e. far from acceptable).

The final sieving and mixing gave a fairly homogeneous mixture (1.6% RSD), but the assay of C21 decreased substantially from 103 to 75%. This decrease was even larger than observed in Comparative Examples 5 and 6 above (i.e. without colloidal silica), which was very surprising.

Similar results were observed for the micronized C21. Again, C21 had a tendency to clump together. Homogeneity increased after 30 minutes of mixing and then decreased with longer mixing times. The assay ended up unexpectedly low (90%). Although the variability decreased steadily with increasing mixing time, it was at best 11% (i.e. far from acceptable).

The final sieving and mixing gave a fairly homogeneous mixture (1.2% RSD), but the assay of C21 had decreased substantially from 90 to 81%. The tendency towards decreasing assay to values below 100% after 60 minutes indicated serious mixing problems.

It was found only to be possible to make anything resembling a homogeneous mixture following extensive mixing followed by a final sieving and mixing.

Comparative Example 9—Changing Vessels

An attempt to ascertain whether the nature of the mixing vessel had any effect on the outcome. C21 and mannitol (Mannogem EZ spray dried) were passed through a 300 μm sieved to remove lumps. The ingredients were added to a polyethylene (PE-HD) jar and mixed as above.

Again, during mixing, it was observed that some lumps had been formed and that the wall and lid was coated with a layer of powder.

The mean value for assay C21 was initially 103% and, again, decreased up to the 60 minutes time point. The variability was big but decreased with increasing mixing time.

The final sieving and mixing gave a homogeneous mixture (0.9% RSD) but, once again, the assay of C21 had decreased substantially (by about 16%), implying that the plastic jar had more of a tendency to adsorb C21 than glass did. Indeed, the walls of the jar including the lid were found to be covered with a layer of powder.

Thus, in summary, C21 sodium salt was found to give rise to an unexpected chemical instability when mixed in the dry state with many conventional excipients. It also has needle-shaped particles, and is sticky, and so tends to clump together, and so it cannot be mixed easily with conventional excipients to give a powder mixture with an acceptable content uniformity.

Additionally, when equipment was used for automated weighing, using an endless screw, the API stuck to the screw and did not fall off in the vials.

Example 10—Dosage Form of the Invention I

An excipient mixture was prepared with a composition comprising mannitol (Pearlitol® 25C (mean particle size diameter 25 μm; Roquette; 247.75 g) and colloidal silicon dioxide (Aerosil Evonik; 0.25 g).

Approximately half of the weighed amount of mannitol was placed into a 3 L V-shell in a V-blender (Dott. Bonapace, Limbiate, Italy), followed by all of the colloidal silicon dioxide. The remaining mannitol was then added to the V-shell, and blending took place for 10 minutes at 30 rpm.

The excipient blend was then sieved through an 800 μm sieve, prior to blending for a further 20 minutes at 30 rpm.

After this, a 500 mL measuring cylinder was weighed, and 100 mL of the respective excipient blend was poured into the cylinder. 50 g of C21 sodium salt (synthesized by Ardena (formerly Syntagon AB), Södertälje, Sweden) was weighed and transferred to the measuring cylinder. The bulk volume ($V_{bulk}$) was read.

Further excipient blend was then added up to 370 mL (on the cylinder). The resultant was gently tapped 10×, further excipient blend was added up to 350 mL to compensate for the volume decrease, followed by gentle tapping 5× (the final volume was 340 mL). The total mass of the filled cylinder was weighed and the bulk density of the mixture (dbulk) was determined as 0.4 g/mL.

The contents of the measuring cylinder were then transferred to a 3 L V-shell of a V-blender, blended for 10 minutes at 30 rpm followed by sieving through a 500 μm sieve and the final blending for 40 minutes at 30 rpm.

It was noticed that the blend adhered to the metal walls of the V-shell and that lumps were formed. It was therefore decided to perform a further sieving step through an 800 μm sieve, and then blend for a further 30 minutes at 30 rpm.

After the blend was prepared, blend uniformity was determined by weighing about 270 mg of blend sample (corresponding to the filling weight of 1 capsule) into a 100 mL volumetric flask, adding 40 mL of MilliQ water and 20 minutes of sonication, adding 40 mL of methanol and sonicating for a further 20 minutes. After equilibrating to room temperature, 1.0 mL of the sample solution was added to a 10 mL volumetric flask. This was followed by diluting with methanol and mixing.

The sample was filtered through a 0.45 μm PTFE membrane syringe filter, and the first 3 mL of the filtrate were discarded. The amount of C21 sodium salt was determined by UHPLC. The resulting solution should contain 0.1 mg/ml of C21 Na-salt (for 100% of the nominal sample concentration).

The blend uniformity results are shown in Table 14 below.

TABLE 14

| Sample | Assay (%, I.c.) |
|--------|-----------------|
| 1 | 98.0 |
| 2 | 95.4 |
| 3 | 99.9 |
| 4 | 96.7 |
| 5 | 96.2 |
| 6 | 97.6 |
| Mean | 97.3 |
| RSD | 1.6 |

Good blend uniformity results (i.e. average assay values between 95.0-105.0%, I.c. and RSD below 2.0%) were observed.

460 capsules (i.e. 3×120 and 1×100; Vcaps® Plus, Size 0, white opaque; Capsugel) were filled secundum artem using a manual Feton® encapsulation device. Weight sorting was done applying a 5% tolerance limit on the net fill weight of a capsule.

The content uniformity is determined using the same UHPLC method as described above (except that capsules were weighed, opened and the contents and shell transferred to the 100 mL volumetric flask).

30 capsules were assessed. Evaluation was performed for n=10 (first 10 capsules measured) and n=30 capsules. The content uniformity results are shown in Table 15 below.

TABLE 15

| Replicate | Assay (%, l.c.) | Replicate | Assay (%, l.c.) | Replicate | Assay (%, l.c.) |
|-----------|-----------------|-----------|-----------------|-----------|-----------------|
| 1 | 98.5 | 11 | 95.3 | 21 | 102.5 |
| 2 | 98.5 | 12 | 95.0 | 22 | 93.4 |
| 3 | 95.8 | 13 | 100.7 | 23 | 94.4 |
| 4 | 96.5 | 14 | 100.5 | 24 | 96.0 |
| 5 | 93.6 | 15 | 94.9 | 25 | 94.3 |
| 6 | 99.7 | 16 | 98.3 | 26 | 98.8 |
| 7 | 97.0 | 17 | 97.1 | 27 | 101.3 |
| 8 | 94.4 | 18 | 93.2 | 28 | 96.4 |
| 9 | 95.0 | 19 | 100.0 | 29 | 92.7 |
| 10 | 101.0 | 20 | 99.1 | 30 | 97.6 |
| n = 10  Mean | 97.1 | | Not Applicable | | |
| SD | 2.3 | | Not Applicable | | |
| RSD | 2.4 | | Not Applicable | | |
| k | 2.4 | | Not Applicable | | |
| AV | 7.0 | | Not Applicable | | |
| n = 30  Mean | | | 97.0 | | |
| SD | | | 2.7 | | |
| RSD | | | 2.8 | | |
| k | | | 2.0 | | |
| AV | | | 6.9 | | |

Acceptable content uniformity results were obtained for both n=10 and n=30.

Example 11—Dosage Form of the Invention II

An excipient mixture was prepared essentially as described in Example 10 above, except that the final proportions of mannitol:silica in the final blend was 99.17:0.83.

After its manufacture, 37.725 g of the excipient blend was weighed and added to the 3 L V-shell of the V-blender. 50 g of C21 sodium salt was then added to the V-shell. A further 37.725 g of the excipient blend was then added to the V-shell, followed by blending for 10 minutes at 30 rpm.

The resultant blend was then sieved twice through an 800 μm sieve, followed by blending for 40 minutes at 30 rpm.

This blend was then sieved through an 800 μm sieve followed by further blending for 15 minutes at 30 rpm.

Blend uniformity was then determined essentially according to the procedure described in Example 10 above. After re-dilution of the initial sample stock solutions of the sample preparations and reanalysis to exclude laboratory (dilution) error, accurate blend uniformity results are shown in Table 16 below.

TABLE 16

| Sample | Assay (%, I.c.) |
|--------|-----------------|
| 1 | 98.0 |
| 2 | 100.4 |
| 3 | 100.3 |
| 4 | 99.8 |
| 5 | 100.1 |
| 6 | 100.7 |
| Mean | 99.9 |
| RSD | 1.0 |

Good blend uniformity results were observed.

Capsules were filled and content uniformity determined using the same UHPLC method as described in Example 10 above. The content uniformity results are shown in Table 17 below.

TABLE 17

| Replicate | Assay (%, l.c.) | Replicate | Assay (%, l.c.) | Replicate | Assay (%, l.c.) |
|-----------|-----------------|-----------|-----------------|-----------|-----------------|
| 1 | 98.0 | 11 | 99.4 | 21 | 98.1 |
| 2 | 98.3 | 12 | 99.0 | 22 | 97.9 |
| 3 | 102.5 | 13 | 99.5 | 23 | 95.1 |
| 4 | 99.5 | 14 | 99.7 | 24 | 95.9 |
| 5 | 101.4 | 15 | 99.5 | 25 | 97.8 |
| 6 | 96.9 | 16 | 99.0 | 26 | 98.4 |
| 7 | 98.4 | 17 | 96.0 | 27 | 100.8 |
| 8 | 100.3 | 18 | 97.4 | 28 | 96.9 |
| 9 | 103.2 | 19 | 96.4 | 29 | 95.5 |
| 10 | 98.4 | 20 | 96.0 | 30 | 99.0 |
| n = 10  Mean | 99.1 | | Not Applicable | | |
| SD | 2.1 | | Not Applicable | | |
| RSD | 2.1 | | Not Applicable | | |
| k | 2.4 | | Not Applicable | | |
| AV | 5.0 | | Not Applicable | | |
| n = 30  Mean | | | 98.5 | | |
| SD | | | 2.0 | | |
| RSD | | | 2.0 | | |
| k | | | 2.0 | | |
| AV | | | 3.9 | | |

Acceptable content uniformity results were obtained for both n=10 and n=30.

Example 12—Composition in Accordance with the Invention I

An excipient blend was prepared by weighing 2.6 g of colloidal silicon dioxide into a weighing boat. 197.4 g of mannitol (Pearlitol® 50C, mannitol from the same supplier with a slightly larger mean particle size diameter (50 μm)) was then weighed and approximately half of that amount was poured into the 3 L V-shell of the V-blender. The weighed amount of glidant was then added to the V-shell, followed by the remaining mannitol. The resultant mixture was blended for 10 minutes at 30 rpm.

The blend was then sieved through an 800 μm sieve, and then returned to the blender for blending for 20 minutes at 30 rpm.

Approximately 75 mL of the excipient blend was added to a pre-weighed 500 mL measuring cylinder. 26.4 g of C21 sodium salt was weighed and added to the measuring cylinder, a further amount of the excipient blended up to 370 mL was then added, followed by gentle tapping 10×. Further excipient blend was added to 350 mL to compensate for the volume decrease, followed by gently tapping 5× (verified final volume is 340 mL).

The total mass of the cylinder with its content was determined and the net mass of the content calculated, before transferring to the 3 L V-shell, blending for 10 minutes at 30 rpm, sieving the resultant blend through a 400 μm sieve and blending for further 20 minutes at 30 rpm.

Based on the above volume determination, the new composition for a 50 mg of C21/capsule is given below in Table 18 below.

TABLE 18

|  | Composition | |
| --- | --- | --- |
| Ingredient | mg/capsule | % w/w |
| C21 sodium salt | 52.8 | 20.44 |
| mannitol (Pearlitol 50C) | 203.38 | 78.73 |
| colloidal silicon dioxide (Aerosil 200) | 2.14 | 0.83 |

Example 13—Composition in Accordance with the Invention II

Essentially the same blending process as described in Example 12 above was used to prepare 120 active capsules from 0.642 g of colloidal silicon dioxide, 61.014 g of mannitol (Pearlitol 50C) and 15.84 g of C21 sodium salt.

After manufacture of the excipient blend, half of it was re-added to the 3 L V-shell, followed by C21, then the remaining excipient blend, and then blending for 10 minutes at 30 rpm, sieving through an 800 μm sieve, and finally further blending for 20 minutes at 30 rpm.

Blend uniformity was determined as described in Example 10 above and the results are shown in Table 19 below.

TABLE 19

| Sample | Assay (%, I.c.) |
| --- | --- |
| 1 | 99.7 |
| 2 | 98.4 |
| 3 | 97.5 |
| 4 | 101.4 |
| 5 | 98.9 |
| 6 | 98.9 |
| Mean | 99.1 |
| RSD | 1.4 |

Blend uniformity results were acceptable. 120 capsules were filled secundum artem using a manual Feton® encapsulation device. Weight sorting was done applying a 5% tolerance limit on the net fill weight of a capsule, and the results were found to be acceptable.

Example 14—Dosage Form of the Invention III (Scaled Up)

10,000 capsules were prepared using essentially the same blending process as described in Example 13 above, using 21.4 g of colloidal silicon dioxide, 2033.8 g of mannitol (Pearlitol 50C) and 528 g of C21 sodium salt (Ardena, Riga, Latvia). A larger V-blender (Multiblender, Pharmatech, UK) with a 25 L V-shell was employed.

Blend uniformity was determined as described in Example 10 above and is shown in Table 20 below.

TABLE 20

| Sample | Assay (%, I.c.) |
| --- | --- |
| 1 | 100.3 |
| 2 | 102.1 |
| 3 | 104.1 |
| 4 | 100.9 |
| 5 | 98.7 |
| 6 | 99.3 |
| Mean | 100.9 |
| RSD | 1.9 |

Blend uniformity results were acceptable.

After this, 26.1 g of magnesium stearate (Ligamed® MF-2-V, Peter Greven, Germany) was sieved through an 800 μm sieve and added to the blend, following by final blending for 15 minutes at 15 rpm.

The final composition is as set out in Table 21 below.

TABLE 21

|  | Composition | |
| --- | --- | --- |
| Ingredient | mg/capsule | % w/w |
| C21 sodium salt | 52.8 | 20.24 |
| mannitol (Pearlitol 50C) | 203.38 | 77.93 |
| colloidal silicon dioxide (Aerosil 200) | 2.14 | 0.82 |
| magnesium stearate (Ligamed MF-2-V) | 2.61 | 1.00 |

Approximately 6,700 capsules were encapsulated using an MG Compact (MG2, Bologna, Italy) with dosators Size 0, in which the following settings were applied: chamber—11 mm; compression—0 mm; powder layer: 30.0 mm.

Weight sorting was done applying a 5% tolerance limit on the net fill weight of a capsule and was found to be 18.6%. After encapsulation the capsules were manually primary packaged in 100 mL high density polyethylene (HDPE) jars with child-resistant, tamper evident caps containing desiccant (56 capsules/jar). A total of 97 jars were produced and labelled for use in a clinical trial.

Example 15—Stability Study of the Dosage Form of the Invention

The capsules obtained in Example 14 above were tested in a study to evaluate the stability in a clinical representative packaging at ICH (International Council of Harmonisation) storage conditions (i) 25° C. and 60% RH (long term storage condition) and (ii) 40° C. and 75% RH (accelerated storage condition).

The stability data is represented in Table 22 below.

TABLE 22

| Condition | Time (M) | C21 parent found vs. label claim (%) | Impurity (%, w/w) | | | | Dissolution Q at 30 mins mean (min-max) |
|---|---|---|---|---|---|---|---|
| | | | 1 | 2 | 3 | Sum | |
| | Initial | 100.8 | 0.16 | 0.16 | <0.10 | 0.32 | 95 (91-98) |
| 25° C. | 1 | 100.0 | 0.21 | 0.16 | 0.10 | 0.46 | 99 (95-102) |
| and | 3 | 100.1 | 0.16 | 0.17 | <0.10 | 0.33 | 95 (94-96) |
| 60% RH | 6 | 99.1 | 0.22 | 0.16 | <0.10 | 0.38 | 104 (102-107) |
| | 12 | 99.7 | 0.17 | 0.14 | <0.10 | 0.31 | 100 (97-103) |
| 40° C. | 1 | 99.6 | 0.21 | 0.16 | <0.10 | 0.37 | 97 (93-104) |
| and | 3 | 99.3 | 0.21 | 0.18 | <0.10 | 0.38 | 95 (91-99) |
| 75% RH | 6 | 100.4 | 0.25 | 0.15 | <0.10 | 0.40 | 101 (96-105) |

No significant changes were observed in the stability results and all results met the applicable acceptance criteria after 12 months storage at 25° C. and 60% RH and 6 months storage at 40° C. and 75% RH.

The invention claimed is:

1. A pharmaceutical formulation that is suitable for peroral administration to the gastrointestinal tract, which formulation comprises a pharmaceutical composition in the form of a particulate mixture comprising solid particles of N-butyloxycarbonyl-3-(4-imidazol-1-ylmethylphenyl)-5-iso-butylthiophene-2-sulfonamide sodium salt, having a weight- or a volume-based mean diameter that is no more than about 100 μm; and, which particles are homogeneously distributed within a blend of carrier particles having a weight- or a volume-based mean diameter that is within about ±75% of the relevant dimension of the solid particles of N-butyloxycarbonyl-3-(4-imidazol-1-ylmethylphenyl)-5-iso-butylthiophene-2-sulfonamide sodium salt, and a glidant, which composition is contained within a capsule that is suitable for such peroral administration.

2. The formulation as claimed in claim 1, wherein the carrier particles comprise a physical mixture of materials selected from one or more carbohydrates, one or more pharmaceutically-acceptable inorganic salts and/or one or more pharmaceutically-acceptable substances that are insoluble or sparingly soluble in water.

3. The formulation as claimed in claim 2, wherein said one or more carbohydrates is/are selected from the group: sugars and sugar alcohols; said one or more pharmaceutically-acceptable inorganic salts comprise sodium chloride; and/or said one or more pharmaceutically-acceptable substances that are insoluble or sparingly soluble in water is/are selected from the group: microcrystalline cellulose, dicalcium phosphate anhydrate, dicalcium phosphate dihydrate, tricalcium phosphate, calcium carbonate, barium sulphate, starch and pre-gelatinised starch.

4. The formulation as claimed in claim 3, wherein said one or more sugars comprise lactose, said one or more sugar alcohols is/are selected from the group: mannitol, sorbitol and xylitol; and/or said one or more pharmaceutically-acceptable substances that are insoluble or sparingly soluble in water is microcrystalline cellulose.

5. The formulation as claimed in claim 1, wherein the capsule is a hard-shell, two-piece capsule.

6. The formulation as claimed in claim 5, wherein the capsule is made from hydroxypropyl methylcellulose.

7. The formulation as claimed in claim 1, wherein the particles of N-butyloxycarbonyl-3-(4-imidazol-1-ylmethylphenyl)-5-iso-butylthiophene-2-sulfonamide sodium salt have a weight- or a volume-based mean diameter that is no more than about 50 μm.

8. The formulation as claimed in claim 7, wherein the particles of N-butyloxycarbonyl-3-(4-imidazol-1-ylmethylphenyl)-5-iso-butylthiophene-2-sulfonamide sodium salt have a weight- or a volume-based mean diameter that is no more than about 20 μm.

9. The formulation as claimed in claim 7, wherein the particles of N-butyloxycarbonyl-3-(4-imidazol-1-ylmethylphenyl)-5-iso-butylthiophene-2-sulfonamide sodium salt have a weight- or a volume-based mean diameter that is no more than about 10 μm.

10. The formulation as claimed claim 1 wherein the carrier particle material comprises mannitol.

11. The formulation as claimed in claim 1, wherein smaller particles of the glidant material coat the carrier particles.

12. The formulation as claimed in claim 1 that is essentially water-free.

13. A method of treatment of an interstitial lung disease, which method comprises the administration of the formulation as defined in claim 1 to a patient in need of such treatment.

14. The method of treatment as claimed in claim 13, wherein the interstitial lung disease is idiopathic pulmonary fibrosis.

15. The method of treatment as claimed in claim 13, wherein the interstitial lung disease is sarcoidosis.

16. The method of treatment as claimed in claim 13, wherein the treatment includes prevention of morbidity and/or mortality in the relevant condition.

17. The method of treatment as claimed in claim 13, wherein the formulation is administered by the peroral route.

* * * * *